United States Patent
Kumar et al.

(10) Patent No.: US 12,305,163 B2
(45) Date of Patent: May 20, 2025

(54) MICROBIAL CONSORTIUM FOR ENHANCING THE METHANE PRODUCTION FROM FEEDSTOCK

(71) Applicant: INDIAN OIL CORPORATION LIMITED, Maharashtra (IN)

(72) Inventors: Manoj Kumar, Faridabad (IN); Mahendra Pratap Singh, Faridabad (IN); Mohana Rao Damacherla, Faridabad (IN); Umish Srivastva, Faridabad (IN); Dheer Singh, Faridabad (IN); Biswapriya Das, Faridabad (IN)

(73) Assignee: INDIAN OIL CORPORATION LIMITED, Mumbai (IN)

( * ) Notice: Subject to any disclaimer, the term of this patent is extended or adjusted under 35 U.S.C. 154(b) by 117 days.

(21) Appl. No.: 16/943,928

(22) Filed: Jul. 30, 2020

(65) Prior Publication Data
US 2021/0079340 A1 Mar. 18, 2021

(30) Foreign Application Priority Data
Sep. 17, 2019 (IN) .............................. 201921037470

(51) Int. Cl.
*C12N 1/20* (2006.01)
*C12P 5/02* (2006.01)

(52) U.S. Cl.
CPC ................ *C12N 1/20* (2013.01); *C12P 5/023* (2013.01); *C12N 2500/02* (2013.01)

(58) Field of Classification Search
None
See application file for complete search history.

(56) References Cited

U.S. PATENT DOCUMENTS

| | | | |
|---|---|---|---|
| 7,888,085 B2 | 2/2011 | Kovacs | |
| 2008/0124775 A1* | 5/2008 | Kovacs | ..................... C02F 3/34 |
| | | | 435/167 |
| 2015/0101375 A1* | 4/2015 | Manilal | ................. C12M 27/06 |
| | | | 71/10 |

FOREIGN PATENT DOCUMENTS

| | | | | |
|---|---|---|---|---|
| CN | 101705199 | | 5/2010 | |
| EP | 0302968 | | 2/1989 | |
| IN | 201621 05611 | * | 2/2018 | .............. C12M 1/00 |

OTHER PUBLICATIONS

Zabranska, J. et al. 2018. Bioconversion of carbon dioxide to methane using hydrogen and hydrogenotrophic methanogens. Biotechnology Advances 36: 707-720; specif. pp. 707, 709 (Year: 2018).*

* cited by examiner

*Primary Examiner* — Adam Weidner
*Assistant Examiner* — Sharon M. Papciak
(74) *Attorney, Agent, or Firm* — Maschoff Brennan

(57) ABSTRACT

An inoculum of microbial consortium containing live microorganisms is described. More particularly, the enviro-tolerant methane-producing microbial consortium and a method for the production of biogas having high methane content from organic wastes and biomass slurries are described. The microbial consortium of the present disclosure produces stable biogas production without any seasonal variation impact.

5 Claims, No Drawings
Specification includes a Sequence Listing.

MICROBIAL CONSORTIUM FOR ENHANCING THE METHANE PRODUCTION FROM FEEDSTOCK

FIELD OF THE INVENTION

The present invention relates to an inoculum of microbial consortium containing live microorganisms. More particularly, the present invention relates to a novel enviro-tolerant methane-producing microbial consortium and a method for the production of biogas having high methane content from organic wastes and biomass slurries.

The sequence listing disclosed herein is included in a text file having the name "SEQUENCE_LISTING_1348IN1231_ST25," created on Jul. 30, 2020, having a size of 28,891 bytes. The foregoing text file is incorporated herein by reference.

BACKGROUND OF THE INVENTION

Biomethanation is a process by which organic matter and biomass residues are decomposed by simultaneous action of various types of microbes like hydrolytic fermentative bacteria, syntrophic $H_2$-producing acetogenic bacteria, and methanogenic bacteria. Biomethanation allows for the reduction of biological oxygen demand; it produces cells and methane which can be used as fuel and it produces no polluting by-products.

Currently, biomethanation processes normally employ sludge from municipal waste treatment plants, sewer, sludge ponds, any other running old biogas plant or adding cattle dung as the source of microorganisms for the anaerobic digestor. However, when new digestors are seeded with sludge or any much source or cattle dung, a long lag phase occurs because it takes time for the microorganisms in the sludge to adapt to the environment. Beside that the sludge contains some non-specific bacteria which do not produce methane but consume the available carbon source and adversely affect the quality and quantity of the produced biogas.

Biogas producing microbes which develop naturally in organic waste due to microbial succession take longer time which is usually 4-12 weeks. In this case the biogas produced is low in quantity and low in quality.

Moreover, country like India where temperature fluctuates to extremes during the year, biogas production comes significantly low during seasonal variation particularly during the extreme winter and extreme summer.

It has also been observed that the microbial activity varies with composition of the feedstock. A microbial population adapted to one type of feedstock is ineffective for feedstock having different composition.

The above mentioned issues can be addressed by using defined and adapted enviro-tolerant microbial consortium which is effective for a broad spectrum of waste substrates. The present invention discloses a well defined and adapted microbial consortium which can work in broad range of temperature, salinity and pH conditions on broad spectrum of the wastes. It obviously would be advantageous to have microbial consortium as starter cultures for the anaerobic biomethanation of a complex waste that did not require a lag phase before producing useful amounts of methane.

EP 0302968 discloses a starter cultures for the anaerobic biomethanation of a lactose-containing substrate such as whey containing live, reproducible cells of *Leuconostoc mesenteroides*, *Desulfovibrio vulgaris*, *Methanosarcina barkeri*, and *Methanobacterium formicicum*. The starter culture reported in the art is specific to lactose containing substrate like whey.

U.S. Pat. No. 7,888,085 disclose a method for increasing biogas production of thermophilic anaerobe system, particularly by employing some microbes like *Caldicellulosiruptor saccharolyticus*. Method disclosed in this prior art is specific for thermophilic anaerobic digestion.

CN 101705199 discloses a microbial composite comprising of *Methanosarcina acetoacidophilum* DSM-NO. 2834, *Methanobacterium formicicum* DSM-No. 1535, *Methanobrevibacter arboriphilicus* DSM-No. 1125, *Methanolobus tindarius* DSM-No. 2278 and *Methanothrix concilii* DSM-No. 6752 for biomethanation. The method of preparation of inoculum disclosed in this prior art is very time consuming and complicated.

SUMMARY OF THE INVENTION

In an aspect of the present disclosure, there is provided a thermophilic, microaerophilic and salinity tolerant microbial consortium for increasing methane production from feedstock in a biogas production system, said consortium comprising:
  (i) acetoclastic methanogens effective to oxidize acetic acid to methane and carbon dioxide;
  (ii) hydrogenotrophic methanogens;
  (iii) methanotrophic archea; and
  (iv) electroactive bacteria.

In an embodiment, the present disclosure provides a thermophilic, microaerophilic and salinity tolerant microbial consortium for increasing methane production from feedstock in a biogas production system, wherein the acetoclastic methanogens is selected from the group consisting of *Desulfovibrio* sp. (IOC-2), *Brevibacterium* sp. (IOC-5), *Methanothermobacter* sp. (IOC-12), *Methanolobus* sp. (IOC-6), *Thermotoga* sp. (IOC-8).

In an embodiment, the present disclosure provides a thermophilic, microaerophilic and salinity tolerant microbial consortium for increasing methane production from feedstock in a biogas production system, wherein the hydrogenotrophic methanogens is selected from the group consisting of *Methanosarcina* sp. (IOC-1), *Clostridium* sp. (IOC-3), *Methanobacterium* sp. (IOC-4) and *Lactobacillus* sp. (IOC-11).

In an embodiment, the present disclosure provides a thermophilic, microaerophilic and salinity tolerant microbial consortium for increasing methane production from feedstock in a biogas production system, wherein the methanotrophic archea is selected from the group consisting of *Methanosaeta* sp. (IOC-7), *Moorella* sp. (IOC-10) and *Lactobacillus* sp. (IOC-11).

In an embodiment, the present disclosure provides a thermophilic, microaerophilic and salinity tolerant microbial consortium for increasing methane production from feedstock in a biogas production system, wherein the electroactive bacteria is *Clostridium* sp. (IOC-3), *Methanosaeta* sp. (IOC-7), *Pyrococcus* sp. (IOC-9) and *Shewanella* sp. MTCC 25020.

In an embodiment, the present disclosure provides a thermophilic, microaerophilic and salinity tolerant microbial consortium for increasing methane production from feedstock in a biogas production system, wherein the microbial consortium also contain additives selected from the group consisting of buffering agents, growth stimulating nutrients, electron donors or a combination thereof.

In an embodiment, the present disclosure provides a thermophilic, microaerophilic and salinity tolerant microbial consortium for increasing methane production from feedstock in a biogas production system, wherein the microbial consortium is effective at a temperature in the range of 5-65° C., pH in the range of 4-10 and salinity in the range of 0-5%.

In an aspect of the present disclosure, there is provided a thermophilic, microaerophilic and salinity tolerant microbial consortium for increasing methane production from feedstock in a biogas production system, said consortium comprising: *Thermotoga* sp. (IOC-8); *Pyrococcus* sp. (IOC-9); *Moorella* sp. (IOC-10); *Brevibacterium* sp. (IOC-5); *Methanolobus* sp. (IOC-6); *Methanosaeta* sp. (IOC-7); *Desulfovibrio* sp. (IOC-2); *Clostridium* sp. (IOC-3); *Methanosarcina* sp. (IOC-1) and *Methanobacterium* sp (IOC-4).

In an embodiment, the present disclosure provides a thermophilic, microaerophilic and salinity tolerant microbial consortium for increasing methane production from feedstock in a biogas production system, wherein the feedstock is selected from the group consisting of biomass, kitchen waste, volatile fatty acids, sewerage, municipal waste, refinery wastewater, petrochemical industry wastewater, sugar industry waste, slaughter house waste, paper and pulp industry waste, refinery ETP biosludge, agricultural residues or a combination thereof.

In an embodiment, the present disclosure provides a thermophilic, microaerophilic and salinity tolerant microbial consortium for increasing methane production from feedstock in a biogas production system, wherein the yield of biogas in a running biogas producing system increases up to 400% when inoculated by a culture of the microbial consortium.

In an embodiment, the present disclosure provides a thermophilic, microaerophilic and salinity tolerant microbial consortium for increasing methane production from feedstock in a biogas production system, wherein the microbial consortium is self propagating in nature and the cell concentration increases from $10^2$ cfu/kg to $10^{12}$ cfu/kg of feedstock in 1-2 hours.

In an embodiment, the present disclosure provides a thermophilic, microaerophilic and salinity tolerant microbial consortium for increasing methane production from feedstock in a biogas production system, wherein the consortium is used in batch wise, semi-continuous or continuous process of biomethanation.

In an embodiment, the present disclosure provides a thermophilic, microaerophilic and salinity tolerant microbial consortium for increasing methane production from feedstock in a biogas production system, wherein the consortium produce biogas having 80-90 mole % methane and less than 10 mole % carbon dioxide.

In another aspect of the present disclosure, there is provided a process for generating a biogas comprising of 80-90 mole % methane from a feedstock, the method comprising the steps of:
(i) providing a feedstock in a biogas fermenting system;
(ii) inoculating the feedstock with a culture comprising microbial consortium as described above, to form an aqueous slurry;
(iii) anaerobically incubating the slurry from step (ii) at a temperature in the range of 5-65° C., pH in the range of 4-10 and salinity in the range of 0-5%;
(iv) collecting biogas containing methane generated in step (iii).

DETAILED DESCRIPTION OF THE INVENTION

Those skilled in the art will be aware that the present disclosure is subject to variations and modifications other than those specifically described. It is to be understood that the present disclosure includes all such variations and modifications. The disclosure also includes all such steps of the process, features of the product, referred to or indicated in this specification, individually or collectively, and any and all combinations of any or more of such steps or features.

Definitions

For convenience, before further description of the present disclosure, certain terms employed in the specification, and examples are collected here. These definitions should be read in the light of the remainder of the disclosure and understood as by a person of skill in the art. The terms used herein have the meanings recognized and known to those of skill in the art, however, for convenience and completeness, particular terms and their meanings are set forth below.

The articles "a", "an" and "the" are used to refer to one or to more than one (i.e., to at least one) of the grammatical object of the article.

The terms "comprise" and "comprising" are used in the inclusive, open sense, meaning that additional elements may be included. It is not intended to be construed as "consists of only".

Throughout this specification, unless the context requires otherwise the word "comprise", and variations such as "comprises" and "comprising", will be understood to imply the inclusion of a stated element or step or group of element or steps but not the exclusion of any other element or step or group of element or steps.

The term "including" is used to mean "including but not limited to". "Including" and "including but not limited to" are used interchangeably.

Unless defined otherwise, all technical and scientific terms used herein have the same meaning as commonly understood by one of ordinary skill in the art to which this disclosure belongs. Although any methods and materials similar or equivalent to those described herein can be used in the practice or testing of the disclosure, the preferred methods, and materials are now described. All publications mentioned herein are incorporated herein by reference.

The present disclosure is not to be limited in scope by the specific embodiments described herein, which are intended for the purposes of exemplification only. Functionally-equivalent products and methods are clearly within the scope of the disclosure, as described herein.

The present disclosure relates to a novel enviro-tolerant methane-producing microbial consortium and its preparation method for the production of methane from organic wastes and biomass slurries.

The object of the present invention is met by optimal combination of high-efficiency strain and developing technology for their rapid propagation.

In this process several bacterial strains were selected and further adapted for their ability to work in wide range of the operating conditions and stable biomethane producing ability. These strains were characterized and combined in a particular ratio to achieve the synergistic and desired outcome. These microbes in consortium included but not limited to following isolates: *Methanosarcina* sp. IOC-1, *Desulfovibrio* sp. IOC-2, *Clostridium* sp. IOC-3, *Methanobacterium* sp. IOC-4, *Brevibacterium* sp. IOC-5, *Methanolobus* sp. IOC-6, *Methanosaeta* sp. IOC-7, *Thermotoga* sp. IOC-8, *Pyrococcus* sp. IOC-9, *Moorella* sp. IOC-10, *Lactobacillus* sp. IOC-11, *Methanothermobacter* sp. IOC-12 etc. The per ml of the inoculum contains cfu $10^6$ of IOC-8, IOC-9 and IOC-10 and/or cfu $10^8$ of IOC-5, IOC-6 and IOC-7 and/or cfu $10^9$ of IOC-2 and IOC-3 and/or cfu $10^{10}$ of IOC-1 and IOC-4. When it is intended to prepare an inoculum the number of cells per ml. can be lower but the microbial composition of the culture should be proportionally equivalent.

These microbes disclosed in present invention have been deposited to IDA approved repository at Microbial Type Culture Collection & Gene Bank (MTCC), Institute of Microbial Technology (IMTECH), Chandigarh, India with following accession number: *Brevibacterium* sp. (IOC-5) MTCC 25255; *Clostridium* sp. (IOC-3) MTCC 25264; *Methanobacterium* sp. (IOC-4) MTCC 25266; *Methanothermobacter* sp. (IOC-12) MTCC 25268; *Methanosarcina* sp. (IOC-1) MTCC 25300; *Desulfovibrio* sp. (IOC-2) MTCC 25301; *Methanolobus* sp. (IOC-6) MTCC 25302; *Methanosaeta* sp. (IOC-7) MTCC 25303; *Thermotoga* sp. (IOC-8) MTCC 25304; *Pyrococcus* sp. (IOC-9) MTCC 25305; *Shewanella* sp. MTCC 25020, *Moorella* sp. (IOC-10) MTCC 25267, *Lactobacillus* sp. (IOC-11) MTCC 25282. The microbial strain *Shewanella* sp. MTCC 25020 was deposited on Apr. 9, 2015. It is a bacterium, Phylum: Pseudomonadota, Class: Gammaproteobacteria, Order: Alteromonadales, Family: Shewanellaceae, Genus: *Shewanella* and Species: *S. putrefaciens*. The microbial strain *Brevibacterium* sp. (IOC-5) MTCC 25255 was deposited on Mar. 1, 2019. It is a bacterium, Phylum: Actinomycetota, Class: Actinomycetia, Order: Micrococcales, Family: Brevibacteriaceae, Genus: *Brevibacterium* and Species: *B. linens*. The microbial strain *Clostridium* sp. (IOC-3) MTCC 25264 was deposited on Apr. 1, 2019. It is a bacterium, Phylum: Bacillota, Class: Clostridia, Order: Eubacteriales, Family: Clostridiaceae, Genus: *Clostridium* and Species *C. thermocellum*. The microbial strain *Methanobacterium* sp. (IOC-4) MTCC 25266 was deposited on Apr. 5, 2019. It is an archaea bacterium, Kingdom: Euryarchaeota, Class: Methanobacteria, Order: Methanobacteriales, Family: Methanobacteriaceae, Genus: *Methanobacterium* and Species: *M. congolense*. The microbial strain *Moorella* sp. (IOC-10) MTCC 25267 was deposited on Apr. 5, 2019. It is a bacterium, Phylum: Bacillota, Class: Clostridia, Order: Moorellales, Family: Moorellaceae, Genus: *Moorella* and species: *M. thermoacetica*. The microbial strain *Methanothermobacter* sp. (IOC-12) MTCC 25268 was deposited on Apr. 5, 2019. It is an archaea bacterium, Kingdom: Euryarchaeota, Class: Methanobacteria, Order: Methanobacteriales, Family: Methanobacteriaceae, Genus: *Methanothermobacter* and Species: *M. thermautotrophicus*. The microbial strain *Lactobacillus* sp. (IOC-11) MTCC 25282 was deposited on May 1, 2019. It is a bacterium, Phylum: Bacillota, Class: Bacilli, Order: Lactobacillales, Family: Lactobacillaceae, Genus: *Lactobacillus* and Species: *L. acetotolerans*. The microbial strain *Methanosarcina* sp. (IOC-1) MTCC 25300 was deposited on Aug. 7, 2019. It is an archaea bacterium, Kingdom: Euryarchaeota, Phylum: Euryarchaeota, Class: Methanomicrobia, Order: Methanosarcinales, Family: Methanosarcinaceae, Genus: *Methanosarcina* and Species: *M. barkeri*. The microbial strain *Desulfovibrio* sp. (IOC-2) MTCC 25301 was deposited on Aug. 7, 2019. It is a bacterium, Phylum: Thermodesulfobacteriota, Class: Desulfovibrionia, Order: Desulfovibrionales, Family: Desulfovibrionaceae, Genus: *Desulfovibrio* and Species: *D. desulfuricans*. The microbial strain *Methanolobus* sp. (IOC-6) MTCC 25302 was deposited on Aug. 7, 2019. It is an archaea bacterium, Kingdom: Euryarchaeota, Phylum: Euryarchaeota, Class: Methanomicrobia, Order: Methanosarcinales, Family: Methanosarcinaceae, Genus: *Methanolobus* and Species: *M. oregonensis*. The microbial strain *Methanosaeta* sp. (IOC-7) MTCC 25303 was deposited on Aug. 7, 2019. It is an archaea bacterium, Kingdom: Euryarchaeota, Phylum: Euryarchaeota, Class: Methanomicrobia, Order: Methanosarcinales, Family: Methanosaetaceae, Genus: *Methanosaeta* and Species: *M. thermoacetophila*. The microbial strain *Thermotoga* sp. (IOC-8) MTCC 25304 was deposited on Aug. 7, 2019. It is a bacterium, Phylum: Thermotogota, Class: Thermotogae, Order: Thermotogales, Family: Thermotogaceae, Genus: *Thermotoga* and Species: *T. naphthophila*. The microbial strain *Pyrococcus* sp. (IOC-7) MTCC 25305 is an archaea bacterium, Kingdom: Euryarchaeota, Phylum: Euryarchaeota, Class: Thermococci, Order: Thermococcales, Family: Thermococcaceae, Genus: *Pyrococcus* and Species: *P. woesei*.

The microbes in consortium included but not limited to following isolates: *Methanosarcina* sp., *Desulfovibrio* sp., *Clostridium* sp., *Methanobacterium* sp., *Brevibacterium* sp., *Methanolobus* sp., *Methanosaeta* sp., *Thermotoga* sp., *Pyrococcus* sp., *Moorella* sp., *Lactobacillus* sp., *Shewanella* sp., *Methanothermobacter* sp. etc. The per ml of the inoculum contains cfu $10^6$ of *Thermotoga* sp., *Pyrococcus* sp. and *Moorella* sp. and/or cfu $10^8$ of *Brevibacterium* sp., *Methanolobus* sp., *Methanosaeta* sp. and/or $10^9$ of *Desulfovibrio* sp., *Clostridium* sp., and/or cfu $10^{10}$ of *Methanosarcina* sp. and *Methanobacterium* sp. When it is intended to prepare an inoculum the number of cells per ml. can be lower, but the microbial composition of the culture should be proportionally equivalent.

In an embodiment, the microbial consortia is effective when applied, relative to the volume of feedstock, in at least $10^3$ cells/ml or gram of the feedstock in the reactor.

In an embodiment, the present disclosure provides a thermophilic, microaerophilic and salinity tolerant methane producing microbial consortium, wherein microbial consortium comprises different combination with various microbes which include but not limited to *Shewanella frigidimarina* ATCC 700753, *Shewanella frigidimarina* DSM 12253, *Shewanella denitrificans* ATCC BAA-1090, *Shewanella denitrificans* DSM-15013, *Shewanella gelidimarina* ATCC-700752, *Shewanella gelidimarina* DSM 12621, *Shewanella* sp. MTCC 25020; *Methanosarcina barkeri* ATCC-43569, *Methanosarcina barkeri* DSM 800, *Methanosarcina siciliae* ATCC-BAA-931, *Methanosarcina siciliae* DSM 3028, *Methanosarcina vacuolata* ATCC-35090, *Methanosarcina vacuolata* DSM 1232, *Methanosarcina mazei* ATCC-43572, *Methanosarcina mazei* DSM 2053, *Methanosarcina thermophila* ATCC-43570, *Methanosarcina thermophila* DSM 1825, *Desulfovibrio termitidis* ATCC-49858, *Desulfovibrio termitidis* DSM 5308, *Desulfovibrio longus* ATCC 51456, *Desulfovibrio longus* DSM 6739, *Desulfovibrio burkinensis* ATCC-700846, *Desulfovibrio burkinensis* DSM 6830, *Desulfovibrio gabonensis* ATCC-700201, *Desulfovibrio gabonensis* DSM 10636, *Desulfovibrio halophilus* ATCC-51179, *Desulfovibrio halophilus* DSM 5663, *Desulfovibrio bastinii* ATCC-BAA-903, *Desulfovibrio bastinii* DSM 16055, *Desulfovibrio magneticus* ATCC-700980, *Desulfovibrio magneticus* DSM 13731, *Desulfovibrio putealis* ATCC-BAA-905, *Desulfovibrio putealis* DSM 16056, *Desulfomicrobium escambiense* ATCC-51164, *Desulfomicrobium escambiense* DSM 10707, *Clostridium bartlettii* ATCC-BAA-827, *Clostridium bartlettii* DSM 16795, *Clostridium carboxidivorans* ATCC-BAA-624, *Clostridium carboxidivorans* DSM 15243, *Clostridium diolis* ATCC-BAA-557, *Clostridium sulfidigenes* ATCC BAA-1538, *Clostridium sulfidigenes* DSM 18982, *Clostridium acidisoli* ATCC-BAA-167, *Clostridium acidisoli* DSM 12555, *Clostridium paradoxum* ATCC-51510, *Clostridium paradoxum* DSM 7308, Clostridium methoxybenzovorans ATCC-700855, Clostridium methoxybenzovorans DSM 12857, Clostridium lacusfryxellense ATCC-BAA-580, Clostridium lacusfryxellense DSM 14205, Clostridium viride ATCC 43977, Clostridium viride DSM 6368, Clostridium thermopalmarium ATCC-51427, Clostridium thermopalmarium DSM 5974, Clostridium hungatei ATCC-700212, Clostridium hungatei DSM 14427, Clostridium psychrophilum ATCC-BAA-582, Clostridium psychrophilum DSM 14207, Clostridium frigoris ATCC-BAA-579, Clostridium frigoris DSM 14204, Clostridium frigidicarnis ATCC-BAA-154, Clostridium frigidicarnis DSM 12271, Clostridium collagenovorans ATCC-49001, Clostridium collagenovorans DSM 3089, Clostridium saccharobutylicum ATCC-BAA-117, Clostridium saccharobutylicum DSM13864, Methanothermobacter defluvii ATCC-51443, Methanothermobacter defluvii DSM 7466, Methanobacterium subterraneum ATCC 700657, Methanobacterium subterraneum DSM 11074, Methanobacterium arbophilicum ATCC-33747, Methanobacterium arbophilicum DSM 1125, Methanobacterium alcaliphilum ATCC-43379, Methanobacterium alcaliphilum DSM 3387, Methanothermobacter wolfeii ATCC-43096, Methanothermobacter wolfeii DSM 2970, Methanothermobacter marburgensis ATCC 43169, Methanothermobacter marburgensis DSM 2133, Methanothermobacter thermoflexus ATCC-51444, Methanothermobacter thermoflexus DSM 7268, Brevibacterium otitidis ATCC-700348, Brevibacterium otitidis DSM 10718, Methanolobus taylorii ATCC BAA 911, Methanolobus taylorii DSM 9005, Methanolobus vulcani ATCC BAA 932, Methanolobus vulcani DSM 3029, Methanolobus tindarius ATCC-35996, Methanolobus tindarius DSM 2278, Methanolobus zinderi ATCC BAA-1601, Methanolobus zinderi DSM 21339, Methanolobus oregonensis ATCC BAA-928, Methanolobus oregonensis DSM 5435, Thermotoga elfii ATCC 51869, Thermotoga elfii DSM 9442, Thermotoga petrophila ATCC BAA 488, Thermotoga petrophila DSM 13995, Thermotoga maritime ATCC 43589, Thermotoga maritime DSM 3109, Thermotoga lettingae ATCC BAA-301, Thermotoga lettingae DSM 14385, Thermotoga naphthophila ATCC-BAA-301, Thermotoga naphthophila DSM 13996, Thermotoga neapolitana ATCC 49049, Thermotoga neapolitana DSM 4359, Pyrococcus horikoshii ATCC 700860, Pyrococcus horikoshii DSM12428, Pyrococcus furiosus ATCC-43587, Pyrococcus furiosus DSM 3638, Pyrococcus woesei ATCC-49860, Pyrococcus woesei DSM 3773, Moorella thermoacetica ATCC 35608, Moorella thermoacetica DSM 521, Moorella mulderi ATCC BAA 608, Moorella mulderi DSM 14980, Lactobacillus camis ATCC 43225, Lactobacillus carnis DSM 20722, Lactobacillus farciminis ATCC 29644, Lactobacillus farciminis DSM 20184, Lactobacillus sanfranciscensis ATCC 27651, Lactobacillus sanfranciscensis DSM 20451, Lactobacillus kefiranofaciens ATCC-51647, Lactobacillus kefiranofaciens DSM 10550, Lactobacillus kefiri ATCC 35411, Lactobacillus kefiri DSM 20587, Lactobacillus minutes ATCC 33267, Lactobacillus minutes DSM 20586, Lactobacillus versmoldensis ATCC BAA-478, Lactobacillus versmoldensis DSM 14857, Lactobacillus aviaries ATCC 43234, Lactobacillus aviaries DSM 20655, Lactobacillus plantarum ATCC BAA-171, Lactobacillus plantarum DSM 13273, Lactobacillus pontis ATCC 51518, Lactobacillus pontis DSM 8475, Methanosaeta concilii DSM 3671, Methanosaeta concilii NBRC 103675, Methanosaeta pelagica DSM 24271, Methanosaeta pelagica NBRC 105920, Methanosaeta harundinacea DSM 17206, Methanosaeta harundinacea NBRC 104789, Methanosaeta thermoacetophila DSM 4774.

In an embodiment of the present disclosure, the biomethanation bioinoculant of the present disclosure comprises several species of microbes; the characteristic of which are given in Table-1 below.

TABLE 1

Characteristics of the microbes may be included in consortium

| Microbes | Shape | Motile | Spore Forming | Gram Stain | Temp. tolerance | Air requirement | Electroactive in nature | Ability to covert CO2 to methane |
|---|---|---|---|---|---|---|---|---|
| Methanosarcina sp. IOC-1 | Irregular spheroid | Non-motile | NO | + | Up to 60° C. | Anaerobic/ Microaerophilic | Yes | No |
| Desulfovibrio sp. IOC-2 | Rod | Motile | NO | (−) | Up to 60° C. | Anaerobic/ Microaerophilic | Yes | No |
| Methanobacterium sp. IOC-4 | Thin Rod | Non-Motile | YES | (+) | Up to 60° C. | Anaerobic | No | Yes |
| Clostridium sp. IOC-3 | Rod | Motile | YES | (+) | Up to 60° C. | Anaerobic | No | Yes |
| Methanothermobacter sp. IOC-12 | Rod | Non-Motile | YES | (+) | Up to 60° C. | Microaerophilic | No | No |
| Brevibacterium sp. IOC-5 | Rod or coccoid | Non-Motile | YES | (+) | Up to 60° C. | Anaerobic/ Microaerophilic | No | No |
| Methanolobus sp. IOC-6 | Irregular coccoid | Non-Motile | YES | (−) | Up to 60° C. | Anaerobic/ Microaerophilic | No | No |
| Thermotoga sp. IOC-8 | Rod | yes | NO | (−) | Up to 60° C. | Anaerobic | No | No |
| Pyrococcus sp. IOC-9 | Irregular coccoid | yes | NO | (−) | Up to 95° C. | Anaerobic | Yes | No |
| Moorella sp. IOC-10 | Rod | Non-motile | YES | (+) | Up to 60° C. | Microaerophilic | Yes | Yes |
| Lactobacillus sp. IOC-11 | Rod | Non-motile | NO | (+) | Up to 60° C. | Microaerophilic | Yes | Yes |
| Methanosaeta sp. IOC-7 | Rod | Non-motile | NO | (−) | Up to 60° C. | Anaerobic/ Microaerophilic | No | Yes |
| Shewanella sp. | Rod | Motile | NO | − | Up to 70° C. | Anaerobic | Yes | Yes |

In an aspect of the present disclosure, there is provided a thermophilic, microaerophilic and salinity tolerant microbial consortium for increasing methane production from feedstock in a biogas production system, said consortium comprising:
(a) acetoclastic methanogens effective to oxidize acetic acid to methane and carbon dioxide;
(b) hydrogenotrophic methanogens;
(c) methanotrophic archea; and
(d) electroactive bacteria.

Biomethanation bioinoculant is a combination of four different microbial groups, viz., Acetoclastic methanogens, Hydrogenotrophic methanogens, Methanotrophic archea and Electro-active bacteria that help in biogas production through different biochemical routes. After the acetogenesis step, methane generation could occur through two different routes, one being direct oxidation of acetic acid to methane using Acetoclastic methanogens, while the other being through reduction of $CO_2$ along with $H_2$ to produce methane using Hydrogenotrophic methanogens. The direct inter-species electron transfer (DIET) between the microbes plays a critical role in methane production from $CO_2$. This can be enabled and boosted by the bacteria that can exchange electrons through its cell membrane and are called electroactive bacteria.

EAB are the microbes that are having ability to exchange (uptake/discharge) electrons with other bacteria or any other conductive medium where they present. A specific method based on oxidation of nano-sized WO3, was adapted for identification of electro-active bacteria. For this, a sandwich plate method was used where the thin layer of agar media was inoculated with designated bacteria and covered with second layer of WO3 dissolved agar media. The bacteria grown in blue color colonies are electro-active in nature. To identify electro-active methanogens, axenic cultures producing methane were selected and tested in sandwich plate. *Clostridium* sp. (IOC-3), *Methanosaeta* sp. (IOC-7) and *Pyrococcus* sp. (IOC-9) were identified through this method and blended in mixed culture. In addition a previously isolated/deposited EAB, *Shewanella* sp. MTCC 25020, was also blended to enhance the property of DIET in bioinoculant.

In an embodiment of the present disclosure, there is provided a thermophilic, microaerophilic and salinity tolerant microbial consortium for increasing methane production from feedstock in a biogas production system, wherein the electroactive bacteria is *Clostridium* sp. (IOC-3), *Methanosaeta* sp. (IOC-7), *Pyrococcus* sp. (IOC-9) and *Shewanella* sp. MTCC 25020.

Further, the higher and complex carbon content present in waste may hinder the microbial growth but the presence of methanogenic archea helps in withstanding the extremely higher organic loading rates. Some of the microbes have dual function, for instance, *Clostridium* sp. (IOC-3) is a hydrogenotrophic methanogen and at the same time it is electro-active in nature.

In an embodiment of the present disclosure, there is provided a thermophilic, microaerophilic and salinity tolerant microbial consortium for increasing methane production from feedstock in a biogas production system, wherein the methanotrophic archea is selected from the group consisting of *Methanosaeta* sp. (IOC-7), *Moorella* sp. (IOC-10) and *Lactobacillus* sp. (IOC-11).

Acetoclastic methanogens are group of microorganisms that carry out the oxidation of acetic acid to methane and $CO_2$. In an embodiment of the present disclosure, there is provided a thermophilic, microaerophilic and salinity tolerant microbial consortium for increasing methane production from feedstock in a biogas production system, wherein the acetoclastic methanogens is selected from the group consisting of *Desulfovibrio* sp. (IOC-2), *Brevibacterium* sp. (IOC-5), *Methanothermobacter* sp. (IOC-12), *Methanolobus* sp. (IOC-6) and *Thermotoga* sp. (IOC-8).

Hydrogenotrophic methanogens are group of microorganisms that combine $CO_2$ and $H_2$, produced as byproduct in small quantities and convert them to methane. In an embodiment of the present disclosure, there is provided a thermophilic, microaerophilic and salinity tolerant microbial consortium for increasing methane production from feedstock in a biogas production system, wherein the hydrogenotrophic methanogens is selected from the group consisting of *Methanosarcina* sp. (IOC-1), *Clostridium* sp. (IOC-3), *Methanobacterium* sp. (IOC-4) and *Lactobacillus* sp. (IOC-11).

In an embodiment of the present invention, at least one microbe of the consortia has improved traits with respect to methane production and such trait was improved by mutagenesis and/or protoplast fusion. The microbial consortium as disclosed in the present invention is effective on the organic waste having biological oxygen demand in the range of 5,000 to 70, 0000 mg/l.

Mutant microbe having ability to produce higher methane content was developed through random multi-round mutagenesis. Mutagenic agents, viz., N-Methyl-N'-nitro-N-nitrosoguanidine (NTG) and Ethyl methanesulfonate (EMS) were used in combination with UV. *Methanosarcina* sp. (IOC-1) was selected for this purpose and after several rounds of mutagenesis and screening of about 3500 mutants, *Methanosarcina* (IOC-1) mutant was isolated having about 2-3 times higher ability of $CO_2$ reduction to methane. This mutant was also blended to the bioinoculant to get a complete/perfect mixture of microbes that can produce higher biogas yields along with high methane content compared to commercial bioinoculants.

The microbes in consortium included but not limited to microbe having more than 98% sequence similarity with the 16S rDNA sequences of the microbes given in the sequence listing.

The composition of this defined microbial consortium is based on purposeful synergistic mixing of species isolated from diverse ecosystems. In an embodiment of the present disclosure, the microbes included in the microbial consortium are anaerobic or microaerophilic in nature.

The microbial consortia disclosed in the present invention has been designed for the biomethanation broad range of feedstock including but not limited to kitchen waste, biomass residue, industrial wastewater, municipal solid waste etc. The microbial consortium can be used as a starter culture in an anaerobic digestor or may be added to already running digester to improve its performance in terms of COD/BOD reduction, higher methane yield, stable gas production, minimum effect of seasonal variation etc.

In an embodiment of the present invention, the microbial consortium may also contain sufficient amounts of essential minerals, growth factors and nutrients to insure the initial growth of the cultures. The microbial consortium of the present invention may also contain, in addition to the microorganisms, buffering agents and growth stimulating nutrients, such as preservatives, if desired.

The microbial consortium disclosed in the present invention may be adsorbed in some solid matrixes like corn cob power, algal residue etc for ease of transport. The large scale production of microbial consortium can be done by using chemostat and cattle dung as sole source of nutrients and energy. The cattle dung is suspended in water in ratio of 1:3 and used it as media. Individual bacteria are grown separately and mixed after growth, in the required ratio. The consortium based on cattle dung provides a suitable low cost media for its growth.

The microbial consortium disclosed in the present invention can supersede the microbes present in the waste material.

The microbial consortium disclosed in the present invention can work in synergy with the microbes present in running biomethanation plant.

In an embodiment of the present disclosure, there is provided a thermophilic, microaerophilic and salinity tolerant microbial consortium for increasing methane production from feedstock in a biogas production system, wherein the yield of biogas in a running biogas producing system increases upto 400% when inoculated by a culture of the microbial consortium.

In an embodiment of the present disclosure, there is provided a thermophilic, microaerophilic and salinity tolerant microbial consortium for increasing methane production from feedstock in a biogas production system, wherein the microbial consortium is grown in large scale in defined media containing carbon, nitrogen, phosphorus, micronutrients using organic and/or inorganic compounds/salts.

The microbial consortium disclosed in the present invention can produce biogas containing biogas having 80-90 mole % methane with less than 10 mole % $CO_2$. For the higher methane content beside the metabolic activity of the selected microbes, in situ conversion of the $CO_2$ to methane is also responsible. The microbial consortium can produce methane more than 99% of the theoretical yield based on BOD content of the waste and 90% based on the COD content of the organic waste.

In an embodiment, the present disclosure provides a microbial consortium for the production of biogas from feedstock wherein the microbial consortium is effective at a temperature in the range of 5-65° C., pH in the range of 4-10 and salinity in the range of 0-5%.

In an embodiment, the present disclosure provides a microbial consortium for the production of biogas from feedstock wherein the feedstock is selected from the group consisting of biomass, kitchen waste, volatile fatty acids, sewerage, municipal waste, refinery wastewater, petrochemical industry wastewater, sugar industry waste, slaughter house waste, paper and pulp industry waste, refinery ETP biosludge, agricultural residues or a combination thereof.

The microbial consortium disclosed in the present invention, contain at least one microbe being electroactive in nature.

The microbial consortium disclosed in the present invention, contains at least one microbe which is having ability to covert $CO_2$ to methane.

The microbial consortium disclosed in the present invention, contains at least one microbe which is having ability to in situ covert $CO_2$ and hydrogen to methane.

The microbial consortium disclosed in the present invention contains at least one microbe which is having ability to in situ bio-transform carbon dioxide to methane.

In an embodiment, the microbial consortium disclosed in the present invention is self propagating in nature. Once, it is present at least $10^2$ cfu/kg of the feedstock, it grows itself and in 1-2 hours reach to the cell concentration of $10^{12}$ cfu/kg of feedstock.

The microbial consortium disclosed in the present invention produces stable biogas production without seasonal variation impact. The microbial consortium is effective in single phase, two phase and three phase biomethanation process.

The microbial consortium can be used in batch wise, semi-continuous or continuous process of biomethanation under septic conditions.

According to one embodiment of the present invention, addition of some electron donor like metal(s) may be part of the consortium.

In another aspect of the present disclosure, there is provided a process for generating biogas comprising of 80-90 mole % methane from a feedstock, the method comprising the steps of:
(i) providing a feedstock in a biogas fermenting system;
(ii) inoculating the feedstock with a culture of microbial consortium comprising live microorganisms selected from the group consisting of acetoclastic methanogens, hydrogenotrophic methanogens, methanotrophic archea and electroactive bacteria to form an aqueous slurry;
(iii) anaerobically incubating the slurry from step (ii) at a temperature in the range of 5-65° C., pH in the range of 4-10 and salinity in the range of 0-5%;
(iv) collecting biogas containing methane generated in step (iii).

Having described the basic aspects of the present invention, the following non-limiting examples illustrate specific embodiment thereof.

EXAMPLES

The disclosure will now be illustrated with working examples, which is intended to illustrate the working of disclosure and not intended to take restrictively to imply any limitations on the scope of the present disclosure. Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods, the exemplary methods, devices and materials are described herein. It is to be understood that this disclosure is not limited to particular methods, and experimental conditions described, as such methods and conditions may vary.

Example 1

Sample Collection: For the purpose of isolation of the microbes, samples were collected from sewage treatment plant, anaerobic digestion reactor and composting site. Anaerobic microbes were isolated by using standard techniques known in the prior art and were selected by their ability to grow at varying temperature of 5-65° C., pH 4-10 and salinity 0-5% on wide range of the feedstock like biomass, kitchen waste, volatile fatty acids, sewerage, municipal waste, refinery wastewater, petrochemical industry wastewater, sugar industry waste, slaughter house waste, paper and pulp industry waste, refinery ETP biosludge, agricultural residues etc.

Selection of substrate: Biomethanation bioinoculant has been evaluated for its efficiency using wide range of organic waste(s) as feedstock. Efficiency of bioinoculant was assessed in both single and two-stage biomethanation and also in comparison with two different commercially used bioinoculants. Further, its efficiency under varying pH, temperature and salinity was also studied. The characteristics of different feedstocks used for evaluation of bioinoculant are given below in Table 2.

TABLE 2

Characteristics of different waste used for evaluation of the biomethanation bioinoculant

| Characteristics | Kitchen waste | MSW | Press mud | Cattle dung | Chicken litter | Biomass | Horticulture waste |
|---|---|---|---|---|---|---|---|
| Bulk density (kg/m3) | 850-910 | 820-910 | 157-201 | 750-820 | 750-850 | 250-350 | 300-400 |
| TS (%) | 22-30 | 25-40 | 25-40 | 18-26 | 18-30 | 85-90 | 55-70 |
| VS (% of TS) | 80-90 | 65-80 | 65-70 | 65-80 | 55-70 | 60-65 | 60-70 |
| Moisture content (%) | 70-80 | 35-60 | 70-75 | 70-85 | 65-75 | 10-15 | 25-40 |
| Organic carbon (TOC) (%) | 12-18 | 12-18 | 15-25 | 8-16 | 6-14 | 40-48 | 22-30 |
| C/N ratio | 16-19 | 40-65 | 12-15 | 3-8 | 2-5 | 140-220 | 80-110 |

Experimental conditions used for evaluation: All the experiments were performed under similar operating conditions to obtain a clear differentiation of the efficiency among the conditions being evaluated. Experiments were performed in bioreactors of 2 L working volume at 40° C. and 100 rpm under anaerobic conditions. For single stage experiments, the feedstock at designated dilution/concentration was filled in bioreactor and pH adjusted to 7.0 and purged with inert gas, nitrogen, to create anaerobic environment followed by addition of designated bioinoculant (10% v/v). For a two-stage experiment, the feedstock at designated dilution/concentration was initially subjected to acidogenic fermentation using acidogenic bacteria followed by collection of leachate. The pH of leachate was adjusted to 7.0 and then subjected to biomethanation using designated bioinoculant. The retention time for both single and two-stage operation varied depending on nature of feedstock. In case of temperature variation experiments, the operating temperature of bioreactor was varied between 0-55° C., keeping all other conditions constant, while operating pH varied from 4-8 in case of experiments for pH variation. All the experiments were conducted in 4-6 sets to identify the variation range as the feedstock is organic waste and its nature varies.

Example 2

Evaluation of Bioinoculant in Comparison to Reference Known Consortiums

The biomethanation bioinoculant was evaluated for its efficiency in comparison with bioinoculant enriched from cattle dung (commonly used inoculum) and bioinoculant obtained from operating large scale anaerobic digester at wastewater treatment unit. All the three biocatalysts evaluated in both single and two-stage biomethanation process using kitchen waste as substrate at a TS loading of 10-12%, the details of results obtained are shown below in Table 3.

TABLE 3

Comparative evaluation of biomethanation bioinoculant against two commercial bioinoculants

| Bioinoculant | % TS removal | | % COD removal | | Biogas yield (m³/Ton) | | Methane yield (m³/Ton) | | Methane content (%) |
|---|---|---|---|---|---|---|---|---|---|
| | Single stage | Two-stage | Single stage | Two-stage | Single stage | Two-stage | Single stage | Two-stage | |
| Bioinoculant developed from cattle dung | 50-56 | 51-62 | 54-60 | 58-65 | 45-60 | 50-65 | 21-30 | 28-35 | 40-55 |
| Bioinoculant from anaerobic digester | 54-64 | 56-60 | 62-68 | 60-65 | 55-65 | 75-85 | 28-35 | 37-46 | 48-60 |
| Biomethanation bioinoculant | 60-66 | 77-82 | 70-75 | 73-77 | 80-100 | 120-140 | 48-58 | 95-110 | 65-84 |

Results: Significantly higher biogas yields (single stage, 80-100 m³/Ton; two-stage, 120-140 m³/Ton) as well as methane content observed by present biomethanation bioinoculant against both the commercial bioinoculants. In addition, methane content in raw biogas is also much higher (65-84 in both single and two stage approaches) in comparison to the commercial bioinoculants, resulting in overall significant higher efficiency of biomethanation bioinoculant. The consortium enriched from cattle dung (most commonly used commercial bioinoculant) has shown just about half of the efficiency of present bioinoculant (single stage, 45-60 m³/Ton; two-stage, 50-65 m³/Ton). Similarly, the bioinoculant from operating large scale bioreactor also showed lower biogas yields (single stage, 55-65 m³/Ton; two-stage, 75-85 m³/Ton). Specifically, there is huge difference in methane content among the bioinoculants and was evident from the methane yield data obtained in two-stage operation. The present consortium is a unique formulation of microbial blend i.e. present methanogenic bioinoculant is a combination of different groups of methanogens that can produce methane through different biochemical routes, resulting in higher biogas yields with high methane content.

Example 3

Synergistic Effect of Different Microbial Groups Used to Prepare Biomethanation Bioinoculant The individual effect of each group of microbes as well as their synergistic interaction was evaluated using exclusion study by avoiding one group of bacteria each time (Table 4). This experiment was carried out in a step-wise approach, where initially the acetoclastic methanogens were not blended in bioinoculant, keeping all other microbial groups. Likewise, further experiments were carried out in sequence by not blending the hydrogenotrophic methanogens, methanotrophic archea and electro-active bacteria. Further to that, a mutant from *Methanosarcina* sp. (IOC-1) was developed through rigorous mutagenesis, which has significant positive impact on biogas generation and added to the consortium to increase the efficiency. All experiments were carried out in two-stage biomethanation process using kitchen waste as substrate at a TS loading of 10-12%.

yields about 10-25% each. Finally, addition of the mutant strain developed through rigorous mutagenesis has shown significant increment, i.e., about 10-15% of biogas yield (120-140 m$^3$/Ton). This has indicated the importance of synergistic interaction of all groups of microbes for producing the higher biogas yields with biomethanation bioinoculant. Further, the ability of bioinoculant in reducing $CO_2$ to methane was also checked by growing the bioinoculant in minimal salt media under purging of $CO_2$:$H_2$:$N_2$ mixture (40:5:55). Microbial growth was distinct along with biogas production indicating the ability of bioinoculant to reduce $CO_2$ to methane.

Example 4

Biomethanation by the Proposed Bioinoculant Using Various Substrates (Feedstocks)

The biomethanation bioinoculant was also evaluated for its feed agnostic nature, i.e., its function with wide range of

TABLE 4

Comprehensive data depicting the synergistic role of different groups of microbes in the present biomethanation bioinoculant

| | % TS removal | % COD removal | Biogas yield (m$^3$/Ton) | Methane yield (m$^3$/Ton) | Biogas yield (m$^3$/Ton TS) | Methane yield (m$^3$/Ton TS) |
|---|---|---|---|---|---|---|
| Without Group-A (Acetoclastic methanogens) | 57-64 | 60-66 | 80-90 | 58-63 | 330-360 | 230-250 |
| Without Group-B (Hydrogenotrophic methanogens) | 64-70 | 70-74 | 85-100 | 50-56 | 350-420 | 180-235 |
| Without Group-C (Methanotrophic archea) | 63-68 | 73-75 | 95-110 | 60-75 | 390-440 | 240-275 |
| Without Group-D (Electro-active bacteria) | 65-73 | 72-77 | 90-115 | 58-77 | 382-415 | 228-264 |
| With all 4 Groups (A, B C and D) | 73-78 | 77-82 | 110-120 | 85-100 | 450-500 | 405-450 |

Results: The unique formulation of microbial blend is combination of different groups of methanogens that produce methane through different biochemical routes. Significantly higher biogas yields as well as methane content observed by the combined bioinoculant of 4 groups (110-120 m$^3$/Ton). The absence of acetoclastic methanogens has reduced the biogas yields to higher extent (80-90 m$^3$/Ton), while the exclusion of hydrogenotrophic methanogens (85-100 m$^3$/Ton) methanotrophic archaea (95-110 m$^3$/Ton) and EAB (90-115 m$^3$/Ton) contributed to reduction of biogas feedstocks. Seven different feedstocks with different substrate nature were selected for evaluation using biomethanation bioinoculant (Table 5). Operating conditions were kept constant as mentioned above and the feedstock dilution was maintained at 1:1 ratio for all feedstocks except biomass waste and horticulture waste, where the dilution ratio was kept at 1:9 and 1:6, respectively, to obtain TS loading rate in similar range with other feedstocks. Experiments were conducted in both single and two-stage approaches and comparatively evaluated.

TABLE 5

Efficiency of biomethanation bioinoculant using different feedstocks

| Feedstock | % TS loading | % TS removal | | % COD removal | | Biogas yield (m$^3$/Ton) | | Methane yield (m$^3$/Ton) | |
|---|---|---|---|---|---|---|---|---|---|
| | | Single stage | Two-stage | Single stage | Two-stage | Single stage | Two-stage | Single stage | Two-stage |
| Kitchen waste (KW) | 10-12 | 60-66 | 77-82 | 70-75 | 73-77 | 70-80 | 120-140 | 48-58 | 95-110 |
| Muncipal Solid Waste (MSW) | 12-14 | 64-68 | 78-82 | 57-63 | 75-78 | 64-72 | 120-140 | 44-52 | 95-110 |
| Press Mud | 14-16 | 68-75 | 77-82 | 78-83 | 75-76 | 80-90 | 140-160 | 57-63 | 110-120 |
| Cattle dung | 9-12 | 68-72 | 73-75 | 66-70 | 85-88 | 46-60 | 100-140 | 32-44 | 75-110 |

TABLE 5-continued

Efficiency of biomethanation bioinoculant using different feedstocks

| Feedstock | % TS loading | % TS removal | | % COD removal | | Biogas yield (m³/Ton) | | Methane yield (m³/Ton) | |
|---|---|---|---|---|---|---|---|---|---|
| | | Single stage | Two-stage | Single stage | Two-stage | Single stage | Two-stage | Single stage | Two-stage |
| Chicken litter | 9-12 | 56-65 | 68-72 | 57-62 | 81-88 | 42-50 | 90-120 | 30-36 | 70-95 |
| Biomass (Paddy straw) | 10-12 | 40-52 | 53-59 | 46-53 | 35-50 | 220-290 | 120-170 | 165-205 | 95-130 |
| Horticulture waste (HW) | 10-12 | 50-56 | 56-62 | 40-54 | 50-57 | 140-180 | 60-80 | 100-130 | 45-62 |

Results: Present bioinoculant has shown biogas yields as well as COD and TS removal efficiency, irrespective of feedstocks. However, two-stage approach yielded higher biogas for all feedstocks except biomass waste and horticulture waste, where the single stage dominated two-stage approach. The results obtained from each feedstock are higher than reported data of any other commercial bioinoculant. Overall, biomass has resulted in higher biogas production (220-290 m3/Ton) followed by horticulture waste (140-180 m³/Ton) and press mud (140-160 m³/Ton). Kitchen waste and MSW has resulted in similar biogas yield (120-140 m³/Ton), while chicken litter (90-120 m³/Ton) and cattle dung (100-140 m³/Ton) has shown least biogas yield. It can be inferred from results that the bioinoculant is feed agnostic in nature and can be used for any type of biodegradable waste in both single and two-stage operations.

Example 5

Efficiency of Bioinoculant Under Wide Range of pH, Temperature and Salinity

Biomethanation bioinoculant can withstand extreme operating conditions like, pH (4-8), temperature (up to 55° C.) and salinity (up to 3000 ppm). To establish this efficiency, individual experiments have been performed for each criterion, keeping all other operational conditions constant, in single stage approach and the results were compared.

Results: The present bioinoculant has shown efficiency to produce biogas between 15-55° C., indicating its thermal stability (Table 6). Optimum temperature for each feedstock is about 30-40° C. except for biomass and horticulture waste, where they produce higher biogas yields around 50° C. Irrespective of the feedstock, the biogas yield increased up to the optimum temperature followed by marginal increment. Impact of temperature on biogas production was studied with respect to easily biodegradable KW and stronger biodegradable biomass waste in single stage approach. At 4° C., there is no biogas production but was increased with increasing temperature (KW, 70-80 m3/Ton at 40° C.; biomass, 277-300 m³/Ton at 50° C.) and further increment in temperature has no significant impact. However, the bioinoculant has survived/functioned between wide range of temperature, i.e. 15-55° C.

TABLE 6

Efficiency of biomethanation bioinoculant under diverse temperature range

| Temperature (° C.) | % TS removal | | % COD removal | | Biogas yield (m³/Ton) | | Methane yield (m³/Ton) | |
|---|---|---|---|---|---|---|---|---|
| | KW | Biomass | KW | Biomass | KW | Biomass | KW | Biomass |
| 4 | 0 | 0 | 0 | 0 | 0 | 0 | 0 | 0 |
| 15 | 14-18 | 7-12 | 18-23 | 10-15 | 17-21 | 49-52 | 12-14 | 33-36 |
| 25 (RT) | 26-38 | 18-23 | 34-47 | 23-28 | 32-48 | 109-121 | 22-33 | 76-85 |
| 30 | 40-51 | 24-28 | 56-70 | 28-33 | 54-67 | 140-160 | 38-47 | 99-114 |
| 40 | 60-66 | 26-33 | 70-75 | 31-37 | 70-80 | 200-224 | 48-58 | 145-160 |
| 50 | 62-70 | 40-52 | 74-79 | 46-53 | 72-80 | 277-303 | 52-58 | 194-212 |
| 55 | 65-72 | 42-54 | 80-84 | 45-54 | 76-82 | 282-305 | 53-58 | 196-212 |

Similar to temperature, bioinoculant has also shown efficiency to perform in a wide range of pH ranging from 4 to 8, indicating its tolerance to extreme operational conditions (Table 7). Optimum operating pH for higher biogas yields is 7 and deviation from that pH has impact on biogas yield and COD removal. The biogas production increased up to pH 7 (KW, 72-81 m3/Ton; biomass, 218-267 m3/Ton) followed by a sudden drop in biogas yield at pH 8 (KW, 32-50 m3/Ton; biomass, 154-190 m3/Ton), however, bioinoculant could withstand its growth in a wide range of pH.

TABLE 7

Efficiency of biomethanation bioinoculant under diverse pH range

| pH | %TS removal | | % COD removal | | Biogas yield (m³/Ton) | | Methane yield (m³/Ton) | |
|---|---|---|---|---|---|---|---|---|
| | KW | Biomass | KW | Biomass | KW | Biomass | KW | Biomass |
| 4 | 12-16 | 5-9 | 14-19 | 6-11 | 12-18 | 28-32 | 7-11 | 16-18 |
| 5 | 19-31 | 16-22 | 29-42 | 21-26 | 29-42 | 87-122 | 21-34 | 51-78 |
| 6 | 38-49 | 21-28 | 53-68 | 27-32 | 52-64 | 142-154 | 37-48 | 89-103 |
| 7 | 60-66 | 40-52 | 70-75 | 31-37 | 72-81 | 218-267 | 49-60 | 142-156 |
| 8 | 42-50 | 27-35 | 44-59 | 36-43 | 32-50 | 154-190 | 22-38 | 104-143 |

TABLE 8

Efficiency of biomethanation bioinoculant under increasing salinity

| Salinity | % TS removal | | % COD removal | | Biogas yield (m³/Ton) | | Methane yield (m³/Ton) | |
|---|---|---|---|---|---|---|---|---|
| (ppm) | KW | Biomass | KW | Biomass | KW | Biomass | KW | Biomass |
| 100 | 61-65 | 38-51 | 69-76 | 30-37 | 71-83 | 220-274 | 48-62 | 145-162 |
| 500 | 59-66 | 39-53 | 72-75 | 31-37 | 69-80 | 214-270 | 46-58 | 144-163 |
| 1000 | 38-49 | 21-28 | 53-68 | 27-32 | 52-64 | 142-154 | 37-48 | 89-103 |
| 1500 | 30-34 | 17-21 | 39-57 | 21-28 | 48-57 | 94-108 | 29-35 | 61-73 |
| 2000 | 23-27 | 14-19 | 33-51 | 17-23 | 41-63 | 68-85 | 24-32 | 42-58 |
| 2500 | 19-31 | 9-16 | 29-42 | 14-19 | 29-42 | 47-61 | 18-25 | 29-36 |
| 3000 | 12-16 | 5-9 | 14-19 | 6-11 | 12-18 | 28-32 | 7-11 | 16-18 |

Biomethanation bioinoculant is a perfect blend of desired, feed agnostic microbes to produce higher biogas yields with higher methane content. The bioinoculant can produce higher biogas in comparison with the commercial bionoculants, irrespective of the feedstock and also delivers higher methane content. Further, the bioinoculant can also sustain to grow and perform at wide range of temperature, pH and salinity. Overall, the microbial blend is a perfect combination of microbes that produce biogas through all possible biochemical routes.

The invention claimed is:

1. A microbial consortium consisting of:

*Thermotoga* sp. MTCC 25304, *Pyrococcus* sp. MTCC 25305, and *Moorella* sp. MTCC 25267, each in a concentration of $10^6$ cfu per ml of the microbial consortium;

*Brevibacterium* sp. MTCC 25255, *Methanolobus* sp. MTCC 25302, and *Methanosaeta* sp. MTCC 25303, each in a concentration of $10^8$ cfu per ml of the microbial consortium;

*Desulfovibrio* sp. MTCC 25301 and *Clostridium* sp. MTCC 25264, each in a concentration of $10^9$ cfu per ml of the microbial consortium;

*Methanosarcina* sp. MTCC 25300 and *Methanobacterium* sp. MTCC 25266, each in a concentration of $10^{10}$ cfu per ml of the microbial consortium; and a mutant obtained through random multi-round mutagenesis of *Methanosarcina* sp. MTCC 25300 using mutagenic agents in combination with ultraviolet (UV), wherein the mutagenic agents comprise N-Methyl-N'-nitro-N-nitrosoguanidine (NTG) and Ethyl methanesulfonate (EMS), wherein the microbial consortium is configured to produce a yield of biogas in a range of 120-140 m$^3$/ton from a feedstock in a biogas production system.

2. The microbial consortium as claimed in claim 1, wherein the microbial consortium is effective at a temperature in a range of 5-65° C., pH in a range of 4-10 and salinity in a range of 0-5%.

3. The microbial consortium as claimed in claim 1, wherein the feedstock is selected from the group consisting of biomass, kitchen waste, volatile fatty acids, sewerage, municipal waste, refinery wastewater, petrochemical industry wastewater, sugar industry waste, slaughterhouse waste, paper and pulp industry waste, refinery Effluent Treatment Plant (ETP) biosludge, agricultural residues, and a combination thereof.

4. The microbial consortium as claimed in claim 1, wherein the microbial consortium increases yield of biogas in a running biogas producing system up to 400% when inoculated by a culture of the microbial consortium.

5. A method for generating biogas from a feedstock, the method consisting of:

(i) providing the feedstock in a biogas fermenting system;

(ii) inoculating the feedstock with a culture comprising the microbial consortium as claimed in claim 1 to form an aqueous slurry;

(iii) anaerobically incubating the aqueous slurry at a temperature in a range of 5-65° C., pH in a range of 4-10 and salinity in a range of 0-5%; and (iv) collecting the biogas generated.

\* \* \* \* \*

SEQUENCE LISTING

<160> NUMBER OF SEQ ID NOS: 14

<210> SEQ ID NO 1
<211> LENGTH: 1410
<212> TYPE: DNA
<213> ORGANISM: Methanosarcina sp IOC-1

<400> SEQUENCE: 1

```
gctatcggtg ttcgcctaag ccatgcgagt catatgttct tcgtgaacat ggcgtactgc      60
tcagtaacac gtggataacc tgcccttggg tctggcataa ccccgggaaa ctggggataa     120
ttccggataa cgcatatatg ctggaatgct ttatgcgtaa aatggattcg tccgcccaag     180
gatgggtctg cggcctatca ggtagtagtg ggtgtaatgt acctactagc ctacaacggg     240
tacgggttgt gagagcaaga gcccggagat ggattctgag acatgaatcc aggaactacg     300
gggcgcaaaa ggcgcgaaaa ctttacgatg cgggaaaccg tgataagggg acaccgagtg     360
ctagcatcat atgctggctg tccaggtgtg taaactacac ctgttagcaa gggccgggca     420
agaccggtgc cagccgccgc ggtaacaccg gcggcccgag tggtgatcgt gattattggg     480
tctaaagggt ccgtagccgg tttggtcagt cctccgggaa atctgatatt tcaactatta     540
ggctttcggg ggatactgcc agacttggaa ccgggagagg taagaggtac tacagggta      600 ggagtgaaat cttgtattcc ctgtgggacc acctgtggcg aaggcgtctt accagaacgg     660
gttcgacggt gagggacgaa agctgggggc acgaaccgga ttagataccc gggtagtccc     720
agccgtaaac gatgctcgct aggtgtcagg catggcgcga ccgtgtctgg tgccgcaggg     780
aagccgtgaa gcgagccacc tgggaagtac ggccgcaagg ctgaaactta aaggaattgg     840
cgggggagca caacaacggg tggagcctgc ggtttaattg gactcaacgc cggacaactc     900
accggggacg acagcaatat gtaggtcagg ctgaagacct tacctgaatc gctgagagga     960
ggtgcatggc cgtcgccagt tcgtactgtg aagcatcctg ttaagtcagg caacgagcga    1020
gacccgtgcc cactgttagc agcatatcct ccgggatgat gggtactctg tggggaccgc    1080
cggtgttaaa tcggaggaag gtgcgggcca cggtaggtca gtatgccccg aatttcccgg    1140
gctacacgcg ggctacaatg aatgggacaa tgggtccctc ccctgaaaag ggctggtaat    1200
ctcacaaacc catcctagt tcggatcgag ggctgtaact cgccctcgtg aagctggaat    1260
ccgtagtaat cgcgtttcaa tatagcgcgg tgaatacgtc cctgctcctt gcacacaccg    1320
```

```
cccgtcaaac cacccgagtg aggtatgggt gagggcacga acatcgtgtc gtgttcgaac    1380
ctgtgctttg caagggggt taagtcgtaa                                      1410

<210> SEQ ID NO 2
<211> LENGTH: 1506
<212> TYPE: DNA
<213> ORGANISM: Desulfovibrio sp IOC-2
<220> FEATURE:
<221> NAME/KEY: misc_feature
<222> LOCATION: (831)..(831)
<223> OTHER INFORMATION: n is a, c, g, or t
<220> FEATURE:
<221> NAME/KEY: misc_feature
<222> LOCATION: (847)..(847)
<223> OTHER INFORMATION: n is a, c, g, or t
<220> FEATURE:
<221> NAME/KEY: misc_feature
<222> LOCATION: (875)..(876)
<223> OTHER INFORMATION: n is a, c, g, or t
<220> FEATURE:
<221> NAME/KEY: misc_feature
<222> LOCATION: (880)..(880)
<223> OTHER INFORMATION: n is a, c, g, or t
<220> FEATURE:
<221> NAME/KEY: misc_feature
<222> LOCATION: (904)..(905)
<223> OTHER INFORMATION: n is a, c, g, or t
<220> FEATURE:
<221> NAME/KEY: misc_feature
<222> LOCATION: (1032)..(1032)
<223> OTHER INFORMATION: n is a, c, g, or t
<220> FEATURE:
<221> NAME/KEY: misc_feature
<222> LOCATION: (1036)..(1036)
<223> OTHER INFORMATION: n is a, c, g, or t
<220> FEATURE:
<221> NAME/KEY: misc_feature
<222> LOCATION: (1135)..(1138)
<223> OTHER INFORMATION: n is a, c, g, or t
<220> FEATURE:
<221> NAME/KEY: misc_feature
<222> LOCATION: (1193)..(1194)
<223> OTHER INFORMATION: n is a, c, g, or t
<220> FEATURE:
<221> NAME/KEY: misc_feature
<222> LOCATION: (1197)..(1198)
<223> OTHER INFORMATION: n is a, c, g, or t
<220> FEATURE:
<221> NAME/KEY: misc_feature
<222> LOCATION: (1480)..(1482)
<223> OTHER INFORMATION: n is a, c, g, or t

<400> SEQUENCE: 2
attgaacgct ggcggcgtgc ctaacacatg caagtcgtgc gtgaaagggc ttcggcctga     60
gtaaagcggc gcacgggtga gtaacgcgtg gatgatctgc ccatgagttg ggaataacgg    120
ctggaaacgg tcgctaatac cgaatacgct ccgatttcat agttcggggg aaaggtggcc    180
tctgcttgca agctaccgct catggatgag tccgcgtccc attagcttgt tggcggggta    240
atggcccacc aaggcgacga tgggtagccg acctgagagg atgatcggcc acactgggac    300
tggaacacgg cccagactcc tacgggaggc agcagtgggg aatattgcgc aatgggcgaa    360
agcctgacgc agcgacgccg cgtgagggat gaaggccttc gggtcgtaaa cctctgtcag    420
gagggaagaa ccgccatggt gctaatcagc catggtctga cggtacctcc aaaggaagca    480
ccggctaact ccgtgccagc agccgcggta atacggaggg tgcaagcgtt aatcggaatc    540
actgggcgta aagcgcacgt aggctgtttg gtaagtcagg ggtgaaatcc cgcagctcaa    600
ctgcgggatt gccctagata ctgctggact tgagttcggg agagggtggc ggaattccag    660
```

```
gtgtaggagt gaaatccgta gatatctgga ggaacatcag tggcgaaggc ggccacctgg      720
accgatactg acgctgaggt gcgaaagcgt ggggagcaaa caggattaga taccctggta      780
gtccacgctg taaacgatgg atgctaggtg tcagggcctt gagcttcggt nccgcagcta      840
acgcgtnaag catcccgcct ggggagtacg gtcgnnaggn tgaaactcaa agaaattgac      900 gggnnccgc acaagcgtgg agtatgtggt ttaattcgat gcaacgcgaa gaaccttacc      960
caggcttgac atccgggaaa ccctcccgaa aaggaggggg ctcttcgga gaatcccgag     1020 acaggtgctg cntggntgtc gtcagctcgt gccgtgaggt gttgggttaa gtcccgcaac     1080
gagcgcaacc cctgttcata gttgctacca ggtaatgctg gcactctat ggagnnnncc     1140 ccggttaacg gggaggaaag tggggatgac gtcaagtcat catggccctt acnnctnngg     1200
ctacacacgt actacaatgg cgcacacaaa gggcagcgat accgtgaggt ggagccaatc     1260
ccaaaaaatg cgtcccagtc cggattgcag tctgcaactc gactgcatga agttggaatc     1320
gctagtaatt cgagatcagc atgctcgggt gaatgcgttc ccgggccttg tacacaccgc     1380
ccgtcacacc acgaaagtcg gttttacccg ataccggtga gccaaccgca aggaggcagc     1440
cgtctacggt agggccgatg attggggtga agtcgtaacn nngtagccgt aggggaacct     1500
gcggct                                                                1506

<210> SEQ ID NO 3
<211> LENGTH: 1268
<212> TYPE: DNA
<213> ORGANISM: Methanobacterium sp IOC-4

<400> SEQUENCE: 3
gctcagtaac acgtggataa cctaccctta ggactgggat aaccctggga aactggggct       60
aatactggat agatggtttt tttcctgtaa tggtatttcg tctaaatgtt tttttcgcc      120 taaggatggg tctgcggccg attaggttgt tggttaggta atggcttacc aagccgttta     180
tcggtacggg ttgtgagagc aagagcccgg agatggaacc tgagacaagg ttccaggccc     240
tacgaggcgc agcaggcgcg aaacctccgc aatgtgagaa atcgcgacgg ggggacccca     300
agtgccattc ttaacgggat ggcttttctt aagtgtaaaa agcttttgga ataagagctg     360
ggcaagaccg gtgccagccg ccgcggtaac accggcagct ctagtggtgg ccagttttat     420
tgggcctaaa gcgttcgtag ccggtttatt aagtctctgg tgaaatcccg tagcttaact     480
atgggaattg ctggagatac tagtagactt gaggtcggga gaggttagag gtactcccag     540
ggtaggggtg aaatcctgta atcctgggag gaccacctgt ggcggaggcg tctaactgga     600
acgaacctga cggtgaggga cgaaagctag gggcgcgaac cggattagat acccgggtag     660
tcctagccgt aaacgatgcg gacttggtgt tagaatggct ttgagccgct ctagtgccga     720
agggaagctg ttaagtccgt cgcctgggaa gtacggtcgc aagactgaaa cttaaaggaa     780
ttggcggggg agcaccacaa cgcgtggagc ctgcggttta attggattca acgccggaca     840
tctcaccagg ggcgacagca gtatgatggc caggttgatg gccttgcttg acaagctgag     900
aggaggtgca tggccgccgt cagctcgtac cgtgaggcgt cctgttaagt caggcaacga     960
gcgagaccca cgcccttagt taccagcgga tccttttttt tggatgccgg gcacactaag    1020
gggaccgcca gtgataaatt ggaggaagga gtggacgacg taggtccgt atgccccgaa     1080 tccctgggc aacacgcggg ctacaatggc tgagacaatg ggtaccgaca ttgaaaagtg    1140
gaggtaatcc tctaaactta gttgtagttc ggattgaggg ctgtaactcg ccctcatgaa    1200
gctggaatgc gtagtaatcg cgtgtcataa tcgcgcggtg aatacgtccc tgctccttgc    1260
```

| acacaccg | 1268 |

<210> SEQ ID NO 4
<211> LENGTH: 1417
<212> TYPE: DNA
<213> ORGANISM: Clostridium sp.IOC-3

<400> SEQUENCE: 4

| tgccggcgtg cttaacacat gcaagtcgag cgatgaagct tcttcggaag tggattagcg | 60 |
| gcggacgggt gagtaacacg tgggtaacct gcctcataga ggggaatagc cttccgaaag | 120 |
| gaagattaat accgcataag attgtaatat cgcatgatat agcgattaaa ggagcaatcc | 180 |
| gctatgagat ggacccgcgt cgcattagct agttggtgag gtaacggctc accaaggcga | 240 |
| cgatgcgtag ccgacctgag agggtgatcg gccacattgg gactgagaca cggcccagac | 300 |
| tcctacggga ggcagcagtg gggaatattg cacaatgggg gaaaccctga tgcagcaacg | 360 |
| ccgcgtgagt gatgacggtc ttcggaaagt aaagctctgt ctttagggac gataatgacg | 420 |
| gtacctaagg aggaagccac ggctaactac gtgccagcag ccgcggtaat acgtaggtgg | 480 |
| caagcgttgt ccggatttac tgggcgtaaa gggagcgtag gtggatattt aagtgggatg | 540 |
| tgaaatactc gggcttaaca tgggtgctgc attccaaact ggatatctag agtgcaggag | 600 |
| aggaaagtag aattcctagt gtagcggtga atgcgtaga gattaggaag aataccagtg | 660 |
| gcgaaggcga ctttctggac tgtaactgac actgaggctc gaaagcgtgg ggagcaaaca | 720 |
| ggattagata ccctggtagt ccacgccgta acgatgaat actaggtgtg ggggttgtca | 780 |
| tgacctccgt gccgccgcta acgcattaag tattccgcct ggggagtacg gtcgcaagat | 840 |
| taaaactcaa aggaattgac gggggcccgc acaagcagcg gagcatgtgg tttaattcga | 900 |
| agcaacgcga agaaccttac ctagacttga catctcctga attactctgt aatagaggaa | 960 |
| gcccttcggg gcaggaagac aggtggtgca tggttgtcgt cagctcgtgt cgtgagatgt | 1020 |
| tgggttaagt cccgcaacga gcgcaaccct tattgttagt tgctaccatt aagttgagca | 1080 |
| ctctagcgag actgcccggg ttaacccggga ggaaggtggg gatgacgtca atcatcatg | 1140 |
| cccccttatgt ctagggctac acacgtgcta caatggctgg tacagagaga tgctaaaccg | 1200 |
| tgaggtggag ccaaacttta aaaccagtct cagttcggat tgtaggctga aactcgccta | 1260 |
| catgaagctg gagttgctag taatcgcgaa tcagaatgtc gcggtgaata cgttcccggg | 1320 |
| ccttgtacac accgcccgtc acaccatgag agttggcaat acccaaagtt cgtgagctaa | 1380 |
| cgcgtaagcg aggcagcgac ctaaggtagg gtcagcg | 1417 |

<210> SEQ ID NO 5
<211> LENGTH: 1444
<212> TYPE: DNA
<213> ORGANISM: Methanothermobacter sp. IOC-12

<400> SEQUENCE: 5

| tcctggcgga ggctactgct aattgggggtt cgaccaagcc atgcaagtcg aacgaacctt | 60 |
| gtgttcgtgg cgaacggctc agtaacacgt ggataacctg cccttgggac cgggataacc | 120 |
| ccgggaaact ggggataaac ctggataggt gatgctgcct ggaatggttc ttcaccgaaa | 180 |
| cacttcgggt gcccaaggat gggtctgcgg ccgattaggt tgttggtagg gtaacggcct | 240 |
| accaagccga tcatcggtac gggttgtgag agcaagagcc ggagatgga acctgagaca | 300 |
| aggttcccag gcctacgggg cgcagcaggc gcgaaacctc cgcaatgcac gcaagtgcga | 360 |

-continued

```
cgggggaacc ccaagtgcca ctcttaacgg ggtggctttt cagaagtgta aaaagcttct     420
ggaataaggg btgggcaaga ccggtgccag ccgccgcggt aacaccggca gctcaagtgg     480
tagccgcttt tattgggcct aaagcgtccg tagccggtct gataagtctc tggtgaaatc     540
ccacagctta actgtgggaa ttgctggaga tactatcaag actcgaggtc gggagaggct     600
ggaggtactc ccagggtagg ggtgaaatcc tgtaatcctg ggaggaccac ctgtggcgaa     660
ggcgtccagc tggaacgaac ctgacggtga gggacgaaag ccaggggcgc gaaccggatt     720
agatacccgg gtagtcctgg ccgtaaacga tgtggacttg gtgttgggat ggcttcgagc     780
tgccccagtg ccgaagggaa gctgttaagt ccaccgcctg ggaagtacgg ccgcaaggct     840
gaaacttaaa ggaattggcg ggggagcacc acaacgcgtg gagcctgcgg tttaattgga     900
ttcaaggccg gacatctcac caggggcgac agcagtatga tggccaggtt gatgaccttc     960
ctgacgagct gagaggaggt gcatggccgc cgtcagctcg taccgtgagg cgtcctgtta    1020
agtcaggcaa cgagcgagac ccacgcccct agttaccagc ggaacccttca tggttgccgg    1080 gcacactaag gggaccgcca gtgatatact ggaggaagga gtggacgacg gtaggtccgt    1140
atgccccgaa tcccctgggc aacacgcggg ctacaatggc ctggacaatg ggttccgaca    1200
ccgaaaggtg gaggtaatcc cctaaaccag gtcgtagttc ggatcgaggg ctgtaacccg    1260
ccctcgtgaa gctggaatgc gtagtaatcg cgtgtcacta tcgcgcggtg aatacgtccc    1320
tgctccttgc acacaccgcc cgtcacgcca cccaaaaagg gcttggatga cggacacaac    1380
acttctgttg tggatcgaat ctgggttctt tgacggacgg cgaacgtcg taacaaggta    1440 gccg                                                               1444
```

<210> SEQ ID NO 6
<211> LENGTH: 1380
<212> TYPE: DNA
<213> ORGANISM: Brevibacterium sp.IOC-5
<220> FEATURE:
<221> NAME/KEY: misc_feature
<222> LOCATION: (278)..(278)
<223> OTHER INFORMATION: n is a, c, g, or t
<220> FEATURE:
<221> NAME/KEY: misc_feature
<222> LOCATION: (297)..(297)
<223> OTHER INFORMATION: n is a, c, g, or t
<220> FEATURE:
<221> NAME/KEY: misc_feature
<222> LOCATION: (359)..(359)
<223> OTHER INFORMATION: n is a, c, g, or t
<220> FEATURE:
<221> NAME/KEY: misc_feature
<222> LOCATION: (362)..(362)
<223> OTHER INFORMATION: n is a, c, g, or t
<220> FEATURE:
<221> NAME/KEY: misc_feature
<222> LOCATION: (470)..(470)
<223> OTHER INFORMATION: n is a, c, g, or t
<220> FEATURE:
<221> NAME/KEY: misc_feature
<222> LOCATION: (1373)..(1373)
<223> OTHER INFORMATION: n is a, c, g, or t

<400> SEQUENCE: 6

```
ctggcggcgt gcttaacaca tgcaagtcga acgctgaagc actgtgcttg cacggtgtgg      60
atgagtggcg aacgggtgag taacacgtga gtaacctgcc cctgacttcg ggataagctt     120
gggaaactgg gtctaatacc ggatgtgact actggccgca tggtctggtg gtggaaaggg     180
ttttactggt tggggatgga ctcgcggcct atcagtttgt tggtgggta gtggcctacc     240 aagacgacga cgggtagccg gcctgacagg gcgaccgncc acactgggac tgagacncgg     300
```

```
cccagactcc tacgggaggc agcagtgggg aatattgcac aatgggggga accctgatnc    360
ancgacgccg cgtgcgggat gacggccttc gggttgtaaa ccgctttcag tagggaagaa    420
gcgaaagtga cggtacctgc agaagaagaa ccggctaact acgtgccagn agccgcggta    480
atacgtaggg tacaagcgtt gtccggaatt attgggcgta aagagctcgt aggtggttgg    540
tcgcgtctgc tgtggaaacg caacgcttaa cgttgcgcgt gcagtgggta cgggctgact    600
agagtgcagt aggggagtct ggaattcctg gtgtagcggt gatatgcgca gatatcagga    660
ggaacaccgg tggcgaaggc gggactctgg gctgtaactg acgctgagga gcgaaagcat    720
ggggagcgaa caggattaga taccctggta gtccatgccg taaacgttgg gaactaggtg    780
tggggtccgt tccacggatt ccgtgccgga gctaacgcat aagttcccc gcctggggag     840
aacggccgca aggctaaaac tcaaaggaat tgacggggc cgcacaagc ggcggagcat      900
gcggattaat tcgatgcaac gcgaagaacc ttaccaaggc ttgacataca ctggaatcgg    960
ctagagatag tcgcgtcttc ggactggtgt acaggtggtg catggttgtc gtcagctcgt   1020
gtcgtgagat gttgggttaa gtcccgcaac gagcgcaacc ctcgttctat gttgccagca   1080
cgtgatggtg ggaactcatg gaagactgcc ggggtcaact cggaggaagg tggggatgac   1140
gtcaaatcat catgcccttt atgtcttggg cttcacgcat gctacaatgg ccggtacaaa   1200
gggtggcgat actgtgaggt ggagcgaatc ccagaaagcc ggtctcagtt cggatcgtag   1260
tctgcaactc gactacgtga agtcggagtc gctagtaatc gaagatcagc aacgctgcgg   1320
tgaatacgtt cccgggcctt gtacacaccg cccgtcaagt cacgaaagtc ggnaacaccc   1380

<210> SEQ ID NO 7
<211> LENGTH: 1480
<212> TYPE: DNA
<213> ORGANISM: Methanolobus sp. IOC-6

<400> SEQUENCE: 7
aattctggtt gatcctgcca gaggttactg ctatcagtgt tcgattaagc catgcgagtc     60
aaatgttctt cgtgaacatg gcgtactgct cagtaacacg tggataaacct gccctaaggt   120
ccggcataac ccccgggaaac tggggataat accggataaa ccatagatac tggaatgttc   180
tgtggtaaaa gttccggcgc cttaggatgg atatgcggcc tatcaggtag tagtgggtgt    240
aaagtaccta ctagccgacg acgggtacgg gttgtgagag caagagcccg gagatggatt   300
ctgagacatg aatccaggcc ctacggggcg cagcaggcgc gaaatctta caatgcggga    360
aaccgcgata aggggacact gagtgccagc atattatgct ggctgtccac ctgtataaat   420
cacaggtgtt agcaagggcc gggcaagacc ggtgccagcc gccgcggtaa caccggcggc   480
ccgagtggta gccactatta ttgggtctaa ccgtccgta gccggtttga tcagtcttcc    540
gggaaatctg acagctcaac tgttaggctt ccggggata ctgtcaggct tgggaccggg    600
agaggtaaga ggtactacag gggtaggagt gaaatcttgt aatccctgtg gaccaccag    660
tggcgaaggc gtcttaccag aacgggtccg acggtgaggg acgaaagctg ggggcacgaa   720
ccggattaga taccgggta gtcccagccg taaacgatgc tcgctaggtg tctgggatgg   780
tgcgaccgtt tcaggtgccg cagggaagcc gtgaagcgag ccacctggga agtacggccg   840
caaggctgaa acttaaagga attggcgggg gagcactaca acgggtggag cctgcggttt    900
aattggactc aacgccggaa aactcacctg gggcgacagc aatatgtagg tcaggctgaa   960
ggtcttacct gaatcgctga gaggaggtgc atggccgtcg tcagttcgta ctgtgaagca  1020
```

-continued

| | |
|---|---|
| tcctgttaag tcaggcaacg agcgagaccc gtgcccactg ttgccagcat atccttcggg | 1080 |
| atgatgggta ctctgtgggg accgctggtg ctaaaccaga ggaaggtgcg ggctacggta | 1140 |
| ggtcagtatg ccccgaatct ccagggctac acgcgggcta caatgaccgg acaatgggc | 1200 |
| tcctaccccg aaagggttg gtaatctcat aaacccggcc gtagttcgga tcgagggctg | 1260 |
| caactcgccc tcgtgaagct ggaatccgta gtaatcgcgt ttcatatagc gcggtgaata | 1320 |
| cgtccctgct ccttgcacac accgcccgtc aaaccaccg agtgaggtat gggtgagggc | 1380 |
| acgaactttg tgtcgtgttc gaacctaaat ttcgcaaggg gggttaagtc gtaacaaggt | 1440 |
| agccgtaggg gaatctgcgg ctggatcacc tcctaagctt | 1480 |

<210> SEQ ID NO 8
<211> LENGTH: 1320
<212> TYPE: DNA
<213> ORGANISM: Thermotoga sp.IOC-7

<400> SEQUENCE: 8

| | |
|---|---|
| agtgaacgct ggcggcgtgc ctaacacatg caagtcgagc gggggaaact cccttcgggg | 60 |
| aggagtaccc agcggcggac gggtgagtaa cacgtgggta acctgccctc ggaggggga | 120 |
| taaccagggg aaaccctggc taataccccca tacgctccat caacgcaagt tggtggagga | 180 |
| aaggggcgtt tgccccgccg gaggaggggc ccgcggccca tcaggtagtt ggtgggtaa | 240 |
| cggcccacca agccgacgac gggtagccgg cctgagaggt tggtcggcca caggggcact | 300 |
| gagacacggg ccccactcct acgggaggca gcagtgggga atcttggaca atgggggaaa | 360 |
| ccctgatcca gcgacgccgc gtgcgggacg aagcccttcg ggtgtaaac cgctgtggcg | 420 |
| ggggaagaat aaagtaggga gggaatgccc taccgatgac ggtaccccgc tagaaagccc | 480 |
| cggctaacta cgtgccagca gccgcggtaa tacgtagggg gcaagcgtta cccggattta | 540 |
| ctgggcgtaa aggggcgta ggcggcctgg tgtgtcggat gtgaaatccc acggctcaac | 600 |
| cgtggggccg catccgaaac taccaggcat ggggcggta gagggagacg gaactgccgg | 660 |
| tgtaggggtg aaatccgtag atatcggcag gaacgccggt ggggaagccg gtctcctggg | 720 |
| ccgaccccga cgctgaggcc cgaaagccag gggagcaaac cggattagat acccgggtag | 780 |
| tcctggccgt aaacgatgcc cactaggtgt ggggggtca tccctccgtg ctgaagctaa | 840 |
| cgcgttaagt gggccgcctg ggagtacgc ccgcaagggt gaaactcaaa ggaattgacg | 900 |
| ggggcccgca caagcggtgg agcgtgtggt ttaattggat gctaagccaa gaaccttacc | 960 |
| agggcttgac atgccggtgg tacctccccg aaagggtag ggaccagtc ctttgggact | 1020 |
| gggagccggc acaggtggtg cacggccgtc gtcagctcgt gccgtgaggt gttgggttaa | 1080 |
| gtcccgcaac gagcgcaacc cctgcccta gttgccagcg gttcggccgg gcactctagg | 1140 |
| gggactgccg gcgacgagcc ggaggaagga ggggatgacg tcaggtactc gtgcccctta | 1200 |
| tgccctgggc gacacacgcg ctacaatggg cggtacaatg ggttgcgacc ccgcgagggg | 1260 |
| gagccaatcc ccaaaaccgc cctcagttcg gatcgcaggc tgcaacccgc ctgcgtgaag | 1320 |

<210> SEQ ID NO 9
<211> LENGTH: 1514
<212> TYPE: DNA
<213> ORGANISM: Thermotoga sp.IOC-8

<400> SEQUENCE: 9

| | |
|---|---|
| gtttgattct cgctcagggt gaacgctggc ggcgtgctta acacatgcaa gtcgcgcggg | 60 |
| gaaaccttcg gggggagtac cagcggcgca cgggtgagta acacgtgggt aacctacccc | 120 |

```
tcagtgggggg ataaccgggg gaaactcccg ctaatacccc atattatccg gtgacgacag    180
ttgctggatg aaaggagtgt tttcttcgct gagggatggg cccgcggccc atcaggtagt    240
tggtgaggta atggctcacc aagcctacga cgggtagccg acctgagagg gtgaccggcc    300
acaagggcac tgagacacgg gcccctactcc tacgggaggc agcagtgggg aattttggac    360
aatgggcgaa agcctgatcc agcgacgccg cgtgagggac gaagccttcg gggtgtaaac    420
ctctgttgtg agggacgaat aagatctgga ggaaatgcca gatcgatgac ggtacctcac    480
gagaaagccc cggctaacta cgtgccagca gccgcggtaa tacgtagggg gcgagcgtta    540
cccgattca ctgggcgtaa aggggcgca ggcgatccag tatgtcgggt gtgaaatccc    600
acagctcaac tgtggaattg cgcccgaaac ttctgggttt ggggctggta gagggagacg    660
gaactgctgg tgtaggggtg aaatccgtag atatcagcag gaacgccggt ggggaagccg    720
gtctcctggg ccaagcccga cgctgaggcc cgaaagctag gggagcaaac cggattagat    780
acccgggtag tcctagccgt aaacgatgcc cactaggtgt gggggagtca ttcctccgtg    840
ctgtagctaa cgcgttaagt gggccgcctg ggagtacgc ccgcaagggt gaaactcaaa    900
ggaattggcg ggaccccgca caagcggtgg agcgtgtggt ttaattggat gctaagccaa    960
gaaccttacc agggcttgac atgcaggtgg taccaacccg aaagggaagg gacccttttcc   1020
ttttggaaag ggagcctgca caggtggtgc acggccgtcg tcagctcgtg ccgtgaggtg   1080
ttgggttaag tcccgcaacg tagcgcaacc cctgccctta gttgccagcg gttcggccgg   1140
gcactctaag ggaccgccg cgacgagcc ggaggaagga ggggacgacg tcaggtactc   1200
gtgccccttta tgccctgggc tacacacgcg ctacaatggg tggtacagtg ggtcgcgacc   1260
tcgcgagagg gagccaatcc ccaaaaccat cctcagttca gatcgcaggc tgcaaccccgc   1320
ctgcgtgaag ccggaatcgc tagtaatcgc ggatcagcca tgccgcggtg aatacgttcc   1380
cggggtttgc acacaccgcc cgtcaagcca cccgagtcgg gggcacctga agacgcctat   1440
cctaacccga aagggaggga aggtgttgaa ggtgaatctg gcgaaggggg ctaagtcgta   1500
acaaggtaac cgta                                                     1514

<210> SEQ ID NO 10
<211> LENGTH: 1260
<212> TYPE: DNA
<213> ORGANISM: Pyrococcus sp. IOC-7

<400> SEQUENCE: 10
atttccggtt gatcctgccg gaggccactg ctatgggggt ccgactaagc catgcgagtc     60
aagggggcgt cccttctggg acgccaccgg cggacggctc agtaacacgt cggtaaccta    120
ccctcgggag ggggataacc ccgggaaact ggggctaatc ccccataggc ctggggtact    180
ggaaggtccc caggccgaaa gggagccgta aggctccgcc cgaggatggg ccggcggccg    240
attaggtagt tggtgggggta acggccacc aagccgaaga tcggtacggg ccgtgagagc    300
gggagcccgg agatggacac tgagacacgg gtccaggccc taccgggcgc agcaggcgcg    360
aaacctccgc aatgcgggaa accgcgacgg ggggaccccc agtgccgtgc ctctggcacg    420
gcttttccgg agtgtaaaaa gctccgggaa taagggctgg gcaaggccgg tggcagccgc    480
cgcggtaata ccggcggccc gagtggtggc cactattatt gggcctaaag cggccgtagc    540
cgggcccgta agtccctcgc gaaatcccac ggctcaaccg tggggctcgc tggggatact    600
gcgggccttg ggaccgggag aggccggggg taccccgggg gtaggggtga atcctataa    660
```

| | |
|---|---|
| tcccgggggg accgccagtg gcgaaggcgc ccggctggaa cgggtccgac ggtgagggcc | 720 |
| gaaggccagg ggagcgaacc ggattagata cccgggtagt cctggctgta aaggatgcgg | 780 |
| gctaggtgtc gggcgagctt cgagctcgcc cggtgccgta gcgaagccgt taagcccgcc | 840 |
| gcctggggag tacggccgca aggctgaaac ttaaaggaat tggcggggga gcactacaag | 900 |
| gggtggagcg tgcggtttat ttggattcaa cgccgggaac ctcaccgggg gcgacggcag | 960 |
| gatgaaggcc aggctgaagg tcttgccgga cgcgccgaga ggaggtgcat ggccgccgtc | 1020 |
| agctcgtacc gtgaggcgtc acttaagtg tggtaacgag cgagacccgc gcccccagtt | 1080 |
| gccagtccct cccgctcggg agggaggcac tctgggggga ctgccggcga taagccggag | 1140 |
| gaagggcgg gcgacggtag gtcagtatgc cccgaaaccc ccgggctaca cgcgcgctac | 1200 |
| aatgggcggg acaatgggac ccgaccccga aggggaagg gaatccccta aacccgccct | 1260 |

<210> SEQ ID NO 11
<211> LENGTH: 1430
<212> TYPE: DNA
<213> ORGANISM: Moorella sp. IOC-10

<400> SEQUENCE: 11

| | |
|---|---|
| agtcgagcgg tctttaattg gggaaatctt cggatggaac cgattaaaga tagcggcgga | 60 |
| cgggtgagta acgcgtgggt aatctaccct tcagactggg ataacaccgg gaaactggtg | 120 |
| ctaataccgg atacggtcta cgggaggcat cttctgtaga agaaaggtgg cgcaagctac | 180 |
| cgctgaagga tgagcccgcg tcccattagc tagttggtga ggtaacggct caccaaggcg | 240 |
| acgatgggta gccggcctga gagggtggtc ggccacactg ggactgagac acggcccaga | 300 |
| ctcctacggg aggcagcagt ggggaatctt gcgcaatggg cgaaagcctg acgcagcaac | 360 |
| gccgcgtgag cgatgaaggc catcgggttg taaacctctg tcatcaggga cgaagtctta | 420 |
| aaggcgaata gcctttaagg tgacggtacc tgaggaggaa gccccggcta actacgtgcc | 480 |
| agcagccgcg gtaaaacgta gggggcgagc gttgtccgga attactgggc gtaaagggcg | 540 |
| tgtaggcggt ctggcaagtc agatgtgaaa accccggct taaccggggg catgcatttg | 600 |
| aaactgccgg gcttgagggc aggagaggag agtggaattc ccgtgtagc ggtgaaatgc | 660 |
| gtagatatcg ggaggaacac cagtggcgaa cgcgactctc tggcctggcc ctgacgctga | 720 |
| ggcgcgaaag cgtggggagc aaacaggatt agataccctg gtagtccacg ccgtaaacga | 780 |
| tgggtactag gtgtaggagg tatcgacccc ttctgtgccg cagtaaacac aataagtacc | 840 |
| ccgcctgggg agtacggccg caaggctgaa actcaaagga attgacgggg cccgcacaa | 900 |
| gcggtggagc atgtggttta attcgacgca acgcgaagaa ccttaccggg gtttgacatc | 960 |
| ctgcgaacct ggtggaaaca ctgggggtgcc catcggggaa cgcagagaca ggtggtgcat | 1020 |
| ggttgtcgtc agctcgtgtc gtgagatgtt gggttaagtc ccgcaacgag cgcaacccct | 1080 |
| accttagtt gccagcgggt aaagccgggc actctaaagg gactgccggt gacaaaccgg | 1140 |
| aggaaggtgg ggatgacgtc aaatcaacat gccccttata tccgggcta cacacgtgct | 1200 |
| acaatggcct gtacaaaggg gtgcgaagga gcgatccgga gcgaatccca aaaagcaggt | 1260 |
| ctcagttcgg attgcaggct gcaactcacc tgcatgaagt cggaatcgct agtaatcgcg | 1320 |
| gatcagcatg ccgcggtgaa tacgttcccg ggccttgtac acaccgcccg tcacaccacg | 1380 |
| aaagttggca cacccgaag ccggtgacct aattcgcgag ggaaggagcc | 1430 |

<210> SEQ ID NO 12
<211> LENGTH: 1261

<212> TYPE: DNA
<213> ORGANISM: Lactobacillus sp. IOC-11
<220> FEATURE:
<221> NAME/KEY: misc_feature
<222> LOCATION: (11)..(12)
<223> OTHER INFORMATION: n is a, c, g, or t

<400> SEQUENCE: 12

```
agagtttgat nntggctcag gacgaacgtt ggcggcgtgc ctaatacatg caagtcgaac    60
gaagtcgccc aattgattct tagtgcttgc actaagatga ttttggatcc gactgagtgg   120
cgaactggtg agtaacacgt gggtaacctg cccagaagaa ggggataaca cctggaaaca   180
gatgctaata ccgtataaca acaagaacca catggttctt gtttgaaagc tggccttgt   240
gctagtgctt ctggatggac ccgcggcgta ttagctagtt ggtgagataa tagctcacca   300
aggcaatgat acgtagcaga cctgagaggg taatctgcca caatgggact gagacacggc   360
ccatactcct acgggaggca gcagtaggga atcttccaca tggacgaaa gtctgatgga   420
gcaacgccgc gtgagtgaag aagggtttcg gctcgtaaaa cactgttgtt agagaagaac   480
agccgtgaga gcaactgctc acggtatgac ggtatctaac cagaaagtca cggctaacta   540
cgtgccagca gccgcggtaa tacgtaggtg caaacgttg tccggattta ttgggcgtaa   600
agggagcgca ggcggtttat taaggctgat gtgaaacgct tcggcttaac cggagaagtg   660
catcggaaac tgataaactt agagtgcaga aaaggatagt cgaacttcat gtgtagcggt   720
gaaatgcgta gatatatgaa ggaacaccag tggcgaaggc ggctatctgg tctgtaactg   780
acgctgaggc tcgaaagcat gggtagcaaa caggattaga taccctggta gtccatgccg   840
taaacgatga atgctaggtg ttggaaggtt ccgcctttc agtgccgcag ctaacgcatt   900
aagcattccg cctggggagt acgaccgcaa ggttgaaact caaaggaatt gacggggacc   960
cgcacaagcg gtggagcatg tggtttaatt cgatgctacg cgaagaacct taccaggact  1020
tgacatcttc tgccaatcta agagattaga cgttccttcg gggacagaat gacaggtggt  1080
gcatggttgt cgtcagctcg tgtcgtgaga tgttgggtta agtcccgcaa cgagcgcaac  1140
ccttgtcttt agttgccagc attaagttgg gcactctaga gagactgccg gtgataaacc  1200
ggaggaaggt ggggatgacg tcaaatcatc atgccccta tgtcctgggc tacacacgtg  1260
c                                                                  1261
```

<210> SEQ ID NO 13
<211> LENGTH: 1407
<212> TYPE: DNA
<213> ORGANISM: Methanosaeta sp. IOC-7

<400> SEQUENCE: 13

```
agaggttact gctatcgagg ttcgactaag ccatgcgagt cgaatgtagc aatacatggc    60
gaactgctca gtaacacgtg gacaacctcc ccttaggacg ggtataaacc cgggaaactg   120
ggtataatac ccgataggtc tcgattgctg gaatgcatcg agatttaaag ctccggcgcc   180
taaggatggg tctgcggcct atcaggtagt agtgggtgta gcgtacctac tagcctacga   240
cgggtacggg ttgtgagagc aagagcccgg agatggattc tgagacacga atccaggccc   300
tacggggtgc agcaggcgcg aaaactttac aatgctggca acagcgataa gggaacctcg   360
agtgccaggt tacaaatctg gctgtcgaga tgcctaaaaa gcatttcata gcaagggccg   420
ggcaagaccg gtgccagccg ccgcggtaac accggcggct cgagtggtaa ccgttattat   480
tgggtctaaa gggtctgtag ccggccggat aagtctcttg agaaatctgg cagcttaact   540
```

-continued

```
gtcaggcttt caggagatac tgtctggcta gatgccggga gaggtgagag gtacttcagg        600
ggtaggggtg aaatcttgta attcttgaag gaccaccagt ggcgaaggcg tctcaccaga        660
acggacctga cggcaaggga cgaaagctag ggcacgaac cggattagat acccgggtag         720
tcctagccgt aaacgatact cgctaggtgt cggccacggt gcgaccgttg tcggtgccgt        780
agggaagccg tgaagcgagc ctcctgggaa gtacggccgc aaggctgaaa cttaaaggaa        840
ttggcggggg agcaccacaa cgggtggagc ttgcggttta attggattca acgccggaaa        900
tcttaccggg accgacagca atatgaaggc caggctgaag actttgccgg attagctgag        960
aggtggtgca tggccgtcgt cagttcgtac tgtgaagcat cctgttaagt caggcaacga       1020
gcgagaccca cgcccacagt tgccagcgta ctctctggag tgacgggtac actgtgggga       1080
ccgccgctgc taaagcggag gaaggaatgg gcaacggtag gtcagtatgc cccgaatatc       1140
ccgggctaca cgcgagctac aatggttggt acaatgggta tctaccccga aaggggacgg       1200
gaatctccta aaaccaatct tagttcggat tgagggctgc aactcgccct catgaagctg       1260
gaatccgtag taatcgcgtt tcaacagaac gcggtgaata cgtccctgct ccttgcacac       1320
accgcccgtc aaaccacccg agtagggtct gaatgagagc gctttctttg gaggcgttcg       1380
aatttgggct ttgcaagggg ggttaag                                           1407
```

<210> SEQ ID NO 14
<211> LENGTH: 1507
<212> TYPE: DNA
<213> ORGANISM: Shewanella sp.

<400> SEQUENCE: 14

```
agagtttgat catggctcag attgaacgct ggcggcaggc ctaacacatg caagtcgagc         60
ggtaacacaa gggcgcttgc tcctgaggtg acgagcggcg gacgggtgag taatacctag        120
gtatctgccc aatcgagggg gataacagtt ggaaacgact gctaataccg catacgccct        180
acggggaaa ggaggggacc ttcgggcctt ccgcgattgg atgaacctag gcggattag         240
ctagttggtg aggtaatggc tcaccaaggc gacgatccct agctggtctg agaggatgat        300
cagccacact ggaactgaga cacggtccag actcctacgg gaggcagcag tggggaatat        360
tgcacaatgg gcgaaagcct gatgcagcca tgccgcgtgt atgaagaagg ccttcgggtt        420
gtaaagtact ttcagcgagg aggaaagctc aagcgttaat agcgcttggg tgtgacgtta        480
ctcgcagaag aagcaccggc taacttcgtg ccagcagccg cggtaatacg aggggtgcaa        540
gcgttaatcg gaattactgg gcgtaaagcg tacgcaggcg gtttgttaag cgagatgtga        600
aagcccnggg ctcaacctgg gaactgcatt tcgaactggc aaactagagt cttgtagagg        660
ggggtagaat ttcaggtgta gcggtgaaat gcgtagagat ctgaaggaat accggtggcg        720
aaggcggccc cctggacaaa gactgacgct catgtacgaa agcgtgggga gcaaacagga        780
ttagataccc tggaagtcca ccccctaaac gatgtctact cggagtttgg tgtcttgaac        840
actgggttct caagctaacg cattaagtag accgcctggg gagtacggcc gcaaggttaa        900
aactcaaatg aattgacggg ggcccgcaca agcggtggag catgtggttt aattcgatgc        960
aacgcgaaga accttaccta ctcttgacat ccacataatt ttccagagat ggattagtgc       1020
cttcgggaac tgtgagacag gtgctgcatg gctgtcgtca gctcgtgttg tgaaatgttg       1080
ggttaagtcc cgcaacgagc gcatccctta tccttatttg ccagcacgta atggtgggaa       1140
ctttaggggag actgccggtg ataaaccgga ggaaggtggg gacgacgtca agtcatcatg      1200
gcccttacga gtagggctac acacgtgcta caatggtcgg tacagagggt cgcaaagccg       1260
```

```
cgaggtgtag ctaatcccac aaagccggtc gtagtccgga tcggagtctg caactcgact    1320
ccgtgaagtc ggaatcgcta gtaatcgtga atcagaatgt cacggtgaat acgttcccgg    1380
gccttgtaca caccgcccgt cacaccatgg gagtgggctg caccagaagt agatagctta    1440
accttcgggg agggcgttta ccacggtgtg gttcatgact ggggtgaagt cgtaacaagg    1500
tagccga                                                              1507
```